United States Patent [19]

Arisawa et al.

[11] Patent Number: 5,322,937
[45] Date of Patent: Jun. 21, 1994

[54] GENES ENCODING A 3-ACYLATION ENZYME FOR MACROLIDE ANTIBIOTICS

[75] Inventors: Akira Arisawa, Fujisawa; Naoto Kawamura, Yamato; Ikuo Kojima, Kawasaki; Kazuhiko Okamura, Fujisawa; Hiroshi Tone, Yokohama; Rokuro Okamoto, Fujisawa, all of Japan

[73] Assignee: Mercian Corporation, Tokyo, Japan

[21] Appl. No.: 708,866

[22] Filed: May 31, 1991

[30] Foreign Application Priority Data

Jun. 1, 1990 [JP] Japan ................................. 1-141625
Feb. 22, 1991 [JP] Japan ................................. 3-048753

[51] Int. Cl.$^5$ .................. C12P 21/06; C12P 19/62; A01N 37/18; C07H 19/00
[52] U.S. Cl. .................. 536/23.7; 435/69.1; 435/76; 435/822; 536/22.1; 536/23.1; 536/23.2
[58] Field of Search ............ 435/76, 69.1, 822; 514/2, 5-21; 536/27, 22.1, 23.1, 23.2, 23.7

[56] References Cited

U.S. PATENT DOCUMENTS 4,201,843  5/1980  Okamoto et al. ................. 435/76

FOREIGN PATENT DOCUMENTS 345546  12/1989  European Pat. Off. .

OTHER PUBLICATIONS

Epp et al., "Production of a hybrid macrolide antibiotic . . . ", Gene, vol. 85, 1989, pp. 293-301.
Tashiro et al., Zoku Seikagaku Jikken Koza (Second Series: Course of Biochemical Experiments), vol. 1, Zdenshi Kenkyuso (Methods of Gene Study) II, 83-104 (1986), ed. by Japan Biochemistry Society.

Primary Examiner—Robert A. Wax
Assistant Examiner—Hyosuk Kim
Attorney, Agent, or Firm—Wenderoth, Lind & Ponack

[57] ABSTRACT

A DNA fragment or a restriction enzyme-digested DNA fragment, the DNA fragment containing a gene, acyA, encoding a 3-acylation enzyme for macrolide antibiotics, characterized by being derived from a strain belonging to the genus Streptomyces, having a size of about 1.8 kb or about 3.2 kb, and having a DNA base sequence shown in a restriction enzyme map shown in FIG. 1(A) or FIG. 1(B), respectively, in the attached drawing. 3-Acylated macrolide antibiotics can be produced advantageously using macrolide antibiotics-producing bacteria transformed with vector plasmids having inserted therein the DNA fragment.

2 Claims, 21 Drawing Sheets

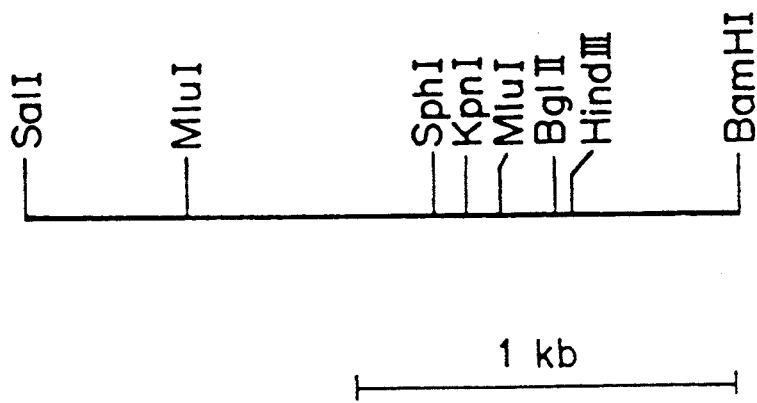
Fig.I(A)
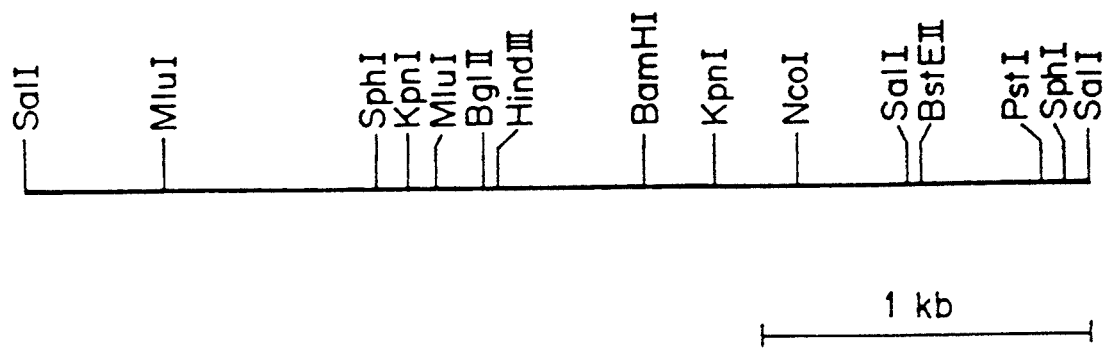
Fig.I(B)

(¹H-NMR OF LEUCOMYCIN A3)

Fig. 6

| | | | | |
|---|---|---|---|---|
| GGATCCATCA | GATTCAAAGC | TGTCATCGTC | CCTGCCCTCC | TCTGAACTGC | CGTCACCACA | 60
| GTGTCAACCG | GACACCGGTG | TCAGGAAAGG | AAAGCGGGCC | TGACTGTGTC | ACCTCCGGGT | 120
| TGCCGGAGAA | ATACCCGGAA | ACCAGGATGG | GCGCGCCCGA | TCTCGGCCGA | CGATTCGGCC | 180
| CCATTTCCAG | CGAAAGGAAC | AAGGATCGAT | GGAGTCGCGC | GTCGAGCGCC | TACCTTCACT | 240
| GACCGGGCTG | CGCTGGTTCG | CGGCGCTTTC | CGTATTCGTC | TGCCATATCG | CCCAGCAGGG | 300
| CATTTTCGCC | GACCCGGACG | TGGCGTCCGC | CCTGGGGCAC | CTCACGTCGC | TCGGCTCGCT | 360
| CGCGGTCTCC | CTCTTCTTCG | TGCTGAGCGG | CTATGTGCTG | ACGTGGTCGG | CCCGGGACGG | 420
| CGACTCCGTC | AGAAGCTTCT | GGCAGCGGTAG | GTTCGCCAAG | ATCTACCCGC | TGCATTTCGT | 480

Fig. 6 continued

```
CACCTTCTGC ATTGCGGGCG TCATCATCTT CAGTCTTTCC GAGCCGGTGC TGCCGGGGCGG    540
TTCGACGTGG GACGGCATGG TGCCCAACCT GCTGCTGGTG CATTCATGGC TGCCGGACGC    600
GTACATCGTC TCGGGATTCA ACACACCGAG CTGGTCGCT TCCTGTGAAA TGGCCTTCTA    660
TCTCACGTTT CCGTTGTGGT ACCGGCTGCT GCTTCGGATA CGGGTGAGCC GGTTGTGGTG    720
GTACGCGGCC GCACTGGCGC TGGCCCGTGGT GTGCATGCCG TTCGTGGCCC GGCTGCTGCC    780
GGACAGCGCG GAGGTCGTTC CCGGGATGCC GCTGCGGGAC ATGTGGTTCA CGTACTGGTT    840
CCCGCCCGTG CGGATGCTGG AGTTCCTCCT CGGCATCGTG CTGGCGCTGA TCCGGGCGCCA    900
GGGGCGTGG CGGGGGCCCG GAACGGGCAC GGCCGGCTG CTGCTCGGGCG GCGGGTTCGC    960
GCTCAACCAG GTGGTGCCGC CGATGTTCAC CCTCACCGCC ACCACCGTCG TCCCCATCGC    1020
```

Fig. 6 continued

```
CCTGCTGATC GCCGCCGCGG CGGACGGGGA TCTGCGCGGG CGCCGTACCG GACTGCCGC    1080
GGCCGTGCTG GTCAGGCTGG GCGAGTGGTC GTACGCCCTC TACCTGATCC ACTTCCTGAT    1140
CATTCGCTAC GGGCACCCGG TGCTGGGGCG CGACCAGGGA TACGCCCGGC AGTGGGACAC    1200
CCTCGCGGCG CTCGGCATCA CAGCGGCGGT ACTGGGGGTC ACGATCGCCG CGAGCGCGGT    1260
CCTGCACATC TTCGTCGAGC GGCCCTGTAT GACCCTGCTG CGCGGCCGCC GCCCTCCGCA    1320
GGGGCCGGCT CCCGACTCCG GGGGCCCGCC GCACCGGGCT CCGCTGGAAA GGGCATGACG    1380
CGTGGCCGAC CAGACCGTTC TCAGTCCCGG ACTGCTGGAA TACGCCAGGA GCGTCTCGCT    1440
GCGCGACGAC GCCGTGCTGC GCGAGCTGCG GGAGTTGACG GCGGCCCTGC CGGGCGGACG    1500
CGCCATGCAG ATCATGCCCGG AGGAGCCCA GCTCCTCGCG CTGCTCATCC GGCTCACGGG    1560
```

Fig. 6 continued

```
CGCCGCCCAG GTCCTGGAGA TCGGCACGTT CACCGGGTAC AGCACGCTGT GCATGGCCCG  1620
GGCACTGCCG CCCGGCGGCC GGATCGTCAC CTGCGACATC ACCGAGCGGT GGCCCGGGCGT  1680
CGGCGCCCCG TTCTGGGCGC AGGCGGGGGT CGCCGACCGC ATCGACCTTC GCATCGGGCGA  1740
CGCCGCCCGG ACCCTGTCCG AGCTGCCGTGC ACACGAAGGC GACGGCATCT TCGACCTGGT  1800
GTTCGTCGAC  1810
```

Fig. 7

```
GGATCCATCA GATTCAAAAGC TGTCATCGTC CCTGCCCTCC TCTGAACTGC CGTCACCACA    60
GTGTCAACCG GACACCGGTG TCAGGAAAAGG AAAGCGGGCC TGACTGTGTC ACCTCCGGGT   120
TGCCGGAGAA ATACCCGGAA ACCAGGATGG GCGCGCCCGA TCTCGGCCGA CGATTCGGCC   180
CCATTTCCAG CGAAAGGAAC AAGGATCG ATG GAG TCG CGC GTC GAG CGC CTA       232
                                Met Glu Ser Arg Val Glu Arg Leu
                                 1               5

CCT TCA CTG ACC GGG CTG CGC TGG TTC GCG GCG CTT TCC GTA TTC GTC     280
Pro Ser Leu Thr Gly Leu Arg Trp Phe Ala Ala Leu Ser Val Phe Val
         10                  15                  20

TGC CAT ATC GCC CAG CAG CAG GGC ATT TTC GCC GAC CCG GAC GTG GCG TCC 328
Cys His Ile Ala Gln Gln Gln Gly Ile Phe Ala Asp Pro Asp Val Ala Ser
     25                  30                  35                  40
```

Fig. 7 continued

```
GCC CTG GGG CAC CTC ACG TCG CTC GGC TCG CTC GCG GTC TCC CTC TTC     376
Ala Leu Gly His Leu Thr Ser Leu Gly Ser Leu Ala Val Ser Leu Phe
                     45                      50                55

TTC GTG CTG AGC GGC TAT GTG CTG ACG TGG TCG GCC CGG GAC GGC GAC     424
Phe Val Leu Ser Gly Tyr Val Leu Thr Trp Ser Ala Arg Asp Gly Asp
                     60                      65                70

TCC GTC AGA AGC TTC TGG CAG CGT AGG TTC GCC AAG ATC TAC CCG CTG     472
Ser Val Arg Ser Phe Trp Gln Arg Arg Phe Ala Lys Ile Tyr Pro Leu
                     75                      80                85

CAT TTC GTC ACC TTC TGC ATT GCG GGC GTC ATC ATC TTC AGT CCT TCC     520
His Phe Val Thr Phe Cys Ile Ala Gly Val Ile Ile Phe Ser Leu Ser
                     90                      95               100
```

Fig. 7 continued

```
GAG CCG GTG CTG CCG GGC GGT TCG ACG TGG GAC GGC ATG GTG CCC AAC    568
Glu Pro Val Leu pro Gly Gly Ser Thr Trp Asp Gly Met Val Pro Asn
105                     110                      115              120

CTG CTG CTG GTG CAT TCA TGG CTG CCG GAC GCG TAC ATC GTC TCG GGA    616
Leu Leu Leu Val His Ser Trp Leu Pro Asp Ala Tyr Ile Val Ser Gly
                125                      130                      135

TTC AAC ACA CCG AGC TGG TCG CTT TCC TGT GAA ATG GCC TTC TAT CTC    664
Phe Asn Thr Pro Ser Trp Ser Leu Ser Cys Glu Met Ala Phe Tyr Leu
             140                      145                      150

ACG TTT CCG TTG TGG TAC CGG CTG CTT CGG ATA CGG GTG AGC CGG        712
Thr Phe Pro Leu Trp Tyr Arg Leu Leu Arg Ile Arg Val Ser Arg
            155                      160                      165
```

Fig. 7 continued

```
TTG TGG TGG TAC GCG GCC GCA CTG GCC CTG GCC GTG GTG TGC ATG CCG    760
Leu Trp Trp Tyr Ala Ala Ala Leu Ala Leu Ala Val Val Cys Met Pro
        170                     175                     180

TTC GTG GCC CGG CTG CTG CCG GAC AGC GCG GAG GTC GTT CCC GGG ATG    808
Phe Val Ala Arg Leu Leu Pro Asp Ser Ala Glu Val Val Pro Gly Met
185                     190                     195             200

CCG CTG CGG GAC ATG TGG TTC ACG TAC TGG TTC CCG CCC GTG CGG ATG    856
Pro Leu Arg Asp Met Trp Phe Thr Tyr Trp Phe Pro Pro Val Arg Met
                205                     210                     215

CTG GAG TTC CTC GGC ATC GTG GCG CTG GCG CTG ATC CGG CGC CAG GGG    904
Leu Glu Phe Leu Gly Ile Val Leu Ala Leu Ile Arg Arg Gln Gly
        220                     225                     230
```

Fig. 7 continued

```
GCG TGG CGG GGG CCC GGA ACG GGC ACG GCC GCG CTG CTC GGC GGC        952
Ala Trp Arg Gly Pro Gly Thr Gly Thr Ala Ala Leu Leu Gly Gly
            235                 240                 245

GCG TTC GCG CTC AAC CAG GTG CCG GTG CCG ATG TTC ACC CTC ACC GCC   1000
Ala Phe Ala Leu Asn Gln Val Pro Val Pro Met Phe Thr Leu Thr Ala
        250                 255                 260

ACC ACC GTC GTC CCC ATC CTG CTG ATC GCC GCG GCG GCG GAC GGC       1048
Thr Thr Val Val Pro Ile Leu Leu Ile Ala Ala Ala Ala Asp Gly
        265                 270                 275         280

GAT CTG CGC GGG CGC ACC GGA CTG CGC GCG GCC GTG CTG GTC AGG       1096
Asp Leu Arg Gly Arg Thr Gly Leu Arg Ala Ala Val Leu Val Arg
            285                 290                 295
```

Fig. 7 continued

```
CTG GGC GAG TGG TCG TAC GCC TTC TAC CTG ATC CAC TTC CTG ATC ATT    1144
Leu Gly Glu Trp Ser Tyr Ala Phe Tyr Leu Ile His Phe Leu Ile Ile
                300                 305                 310

CGC TAC GGG CAC CGG CTG CTG GGC GAC CAG GGA TAC GCC CGG CAG         1192
Arg Tyr Gly His Arg Leu Leu Gly Asp Gln Gly Tyr Ala Arg Gln
            315                 320                 325

TGG GAC ACC CTC GCG GCG CTC GGC ATC ACA GCG GCG GTA CTG GGG GTC    1240
Trp Asp Thr Leu Ala Ala Leu Gly Ile Thr Ala Ala Val Leu Gly Val
        330                 335                 340

ACG ATC GCC GCG AGC GCG GTC CTG CAC ATC TTC GTC GAG CGG CCC TGT    1288
Thr Ile Ala Ala Ser Ala Val Leu His Ile Phe Val Glu Arg Pro Cys
345                 350                 355                 360
```

Fig. 7 continued

```
ATG ACC CTG CTG CGC GGC CGC CCT CCG CAG GGG CCG GCT CCC GAC      1336
Met Thr Leu Leu Arg Gly Arg Arg Pro Pro Gln Gly Pro Ala Pro Asp
                365                 370                 375

TCC GGG GGC CGC CCG CAC CGG GCT CCG CTG GAA AGG GCA TGACGCGTGG   1385
Ser Gly Gly Arg Pro His Arg Ala Pro Leu Glu Arg Ala
                380                 385

CCGACCAGAC CGTTCTCAGT CCGGCACTGC TGGAATACGC CAGGAGCCGTC TCGCTGCGCG   1445
ACGACGCCGT GCTGCGCGAG CTGCGGGAGT TGACGGCGGC CCTGCCGGGC GGACGCGCCA   1505
TGCAGATCAT GCCGGAGGAG GCCCAGCTCC TCGGCGCTGCT CATCCGGCTC ACGGGCGCCG   1565
CCCAGGTCCT GGAGATCGGC ACGTTCACCG GGTACAGCAC GCTGTGCATG GCCCGGGCAC   1625
TGCCGCCCGG CGGCCGGATC GTCACCTGCG ACATCACCGA GCGGTGGCCC GGCGTCGGCG   1685
CCCCGTTCTG GCGGCAGGCG GGGTCGCCG ACCGCATCGA CCTTCGCATC GGCGACGCCG    1745
CCCGGACCCT GTCCGAGCTG CGTGCACACG AAGGCGACGG CATCTTCGAC CTGGTGTTCG   1805
TCGAC                                                               1810
```

$^1$H-NMR OF 3-O-ACETYLTYLOSIN

¹H-NMR OF 3-O-ACETYL-4″-O-ISOVALERYLTYLOSIN

Fig. 13
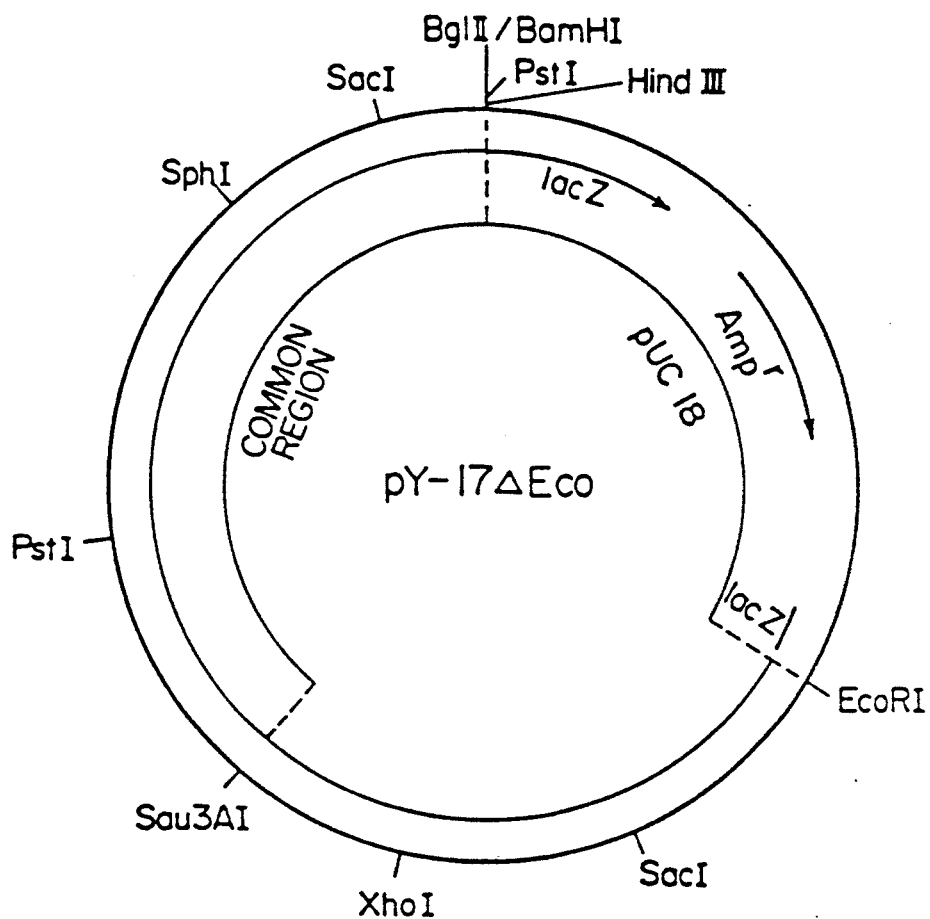
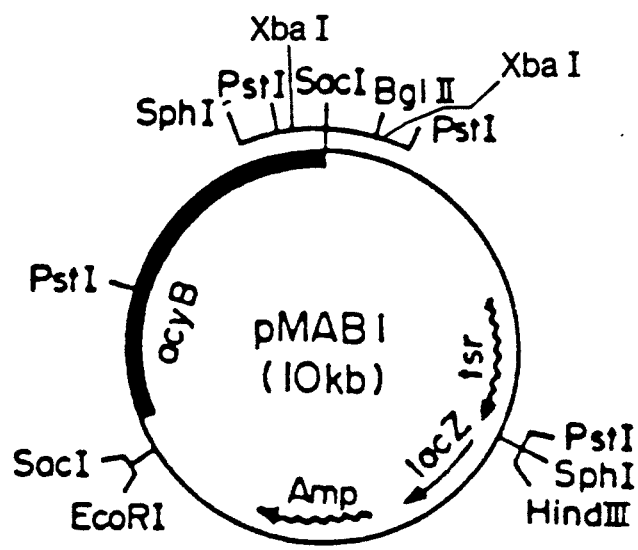
Fig. 14

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1810 base pairs
        ( B ) TYPE: Nucleic acid
        ( C ) STRANDEDNESS: double
        ( D ) TOPOLOGY: linear ( i i ) MOLECULE TYPE: Genomic DNA ( i i i ) HYPOTHETICAL: No ( i v ) ANTI-SENSE: No ( v i ) ORIGINAL SOURCE:
        ( A ) ORGANISM: Streptomyces thermotolerans
        ( B ) STRAIN: ATCC 11416

( i x ) FEATURE:
        ( A ) NAME/KEY: -35 signal
        ( B ) LOCATION: 120..125
        ( C ) IDENTIFICATION METHOD: S ( i x ) FEATURE:
        ( A ) NAME/KEY: -10 signal
        ( B ) LOCATION: 143..148
        ( C ) IDENTIFICATION METHOD: s ( i x ) FEATURE:
        ( A ) NAME/KEY: RBS
        ( B ) LOCATION: 194..198 AND 201..205
        ( C ) IDENTIFICATION METHOD: S ( x i ) SEQUENCE DESCRIPTION: SEQ ID NO:1:

```
GGATCCATCA GATTCAAAGC TGTCATCGTC CCTGCCCTCC TCTGAACTGC CGTCACCACA    60

GTGTCAACCG DACACCGGTG TCAGGAAAGG AAAGCGGGCC TGACTGTGTC ACCTCCGGGT   120

TGCCGGAGAA ATACCCGGAA ACCAGGATGG GCGCGCCCGA TCTCGGCCGA CGATTCGGCC   180

CCATTTCCAG CGAAAGGAAC AAGGATCGAT GGAGTCGCGC GTCGAGCGCC TACCTTCACT   240

GACCGGGCTG CGCTGGTTCG CGGCGCTTTC CGTATTCGTC TGCCATATCG CCCAGCAGGG   300

CATTTTCGCC GACCCGGACG TGGCGTCCGC CCTGGGGCAC CTCACGTCGC TCGGCTCGCT   360

CGCGGTCTCC CTCTTCTTCG TGCTGAGCGG CTATGTGCTG ACGTGGTCGG CCCGGGACGG   420

CGACTCCGTC AGAAGCTTCT GGCAGCGTAG GTTCGCCAAG ATCTACCCGC TGCATTTCGT   480

CACCTTCTGC ATTGCGGGCG TCATCATCTT CAGTCTTTCC GAGCCGGTGC TGCCGGGCGG   540

TTCGACGTGG GACGGCATGG TGCCCAACCT GCTGCTGGTG CATTCATGGC TGCCGGACGC    600

GTACATCGTC TCGGGATTCA ACACACCGAG CTGGTCGCTT TCCTGTGAAA TGGCCTTCTA   660

TCTCACGTTT CCGTTGTGGT ACCGGCTGCT GCTTCGGATA CGGGTGAGCC GGTTGTGGTG   720

GTACGCGGCC GCACTGGCGC TGGCCGTGGT GTGCATGCCG TTCGTGGCCC GGCTGCTGCC   780

GGACAGCGCG GAGGTCGTTC CCGGGATGCC GCTGCGGGAC ATGTGGTTCA CGTACTGGTT   840
```

| | | | | |
|---|---|---|---|---|
| CCCGCCCGTG | CGGATGCTGG | AGTTCCTCCT | CGGCATCGTG | CTGGCGCTGA TCCGGCGCCA | 900 |
| GGGGGCGTGG | CGGGGGCCCG | GAACGGGCAC | GGCCGCGCTG | CTGCTCGGCG GCGCGTTCGC | 960 |
| GCTCAACCAG | GTGGTGCCGC | CGATGTTCAC | CCTCACCGCC | ACCACCGTCG TCCCCATCGC | 1020 |
| CCTGCTGATC | GCCGCCGCGG | CGGACGGCGA | TCTGCGCGGG | CGCCGTACCG GACTGCGCGC | 1080 |
| GGCCGTGCTG | GTCAGGCTGG | GCGAGTGGTC | GTACGCCTTC | TACCTGATCC ACTTCCTGAT | 1140 |
| CATTCGCTAC | GGGCACCGGC | TGCTGGGCGG | CGACCAGGGA | TACGCCCGGC AGTGGGACAC | 1200 |
| CCTCGCGGCG | CTCGGCATCA | CAGCGGCGGT | ACTGGGGGTC | ACGATCGCCG CGAGCGCGGT | 1260 |
| CCTGCACATC | TTCGTCGAGC | GGCCCTGTAT | GACCCTGCTG | CGCGGCCGCC GCCCTCCGCA | 1320 |
| GGGGCCGGCT | CCCGACTCCG | GGGGCCGCCC | GCACCGGGCT | CCGCTGGAAA GGGCATGACG | 1380 |
| CGTGGCCGAC | CAGACCGTTC | TCAGTCCGGC | ACTGCTGGAA | TACGCCAGGA GCGTCTCGCT | 1440 |
| GCGCGACGAC | GCCGTGCTGC | GCGAGCTGCG | GGAGTTGACG | GCGGCCCTGC CGGGCGGACG | 1500 |
| CGCCATGCAG | ATCATGCCGG | AGGAGGCCCA | GCTCCTCGCG | CTGCTCATCC GGCTCACGGG | 1560 |
| CGCCGCCCAG | GTCCTGGAGA | TCGGCACGTT | CACCGGGTAC | AGCACGCTGT GCATGGCCCG | 1620 |
| GGCACTGCCG | CCCGGCGGCC | GGATCGTCAC | CTGCGACATC | ACCGAGCGGT GGCCCGGCGT | 1680 |
| CGGCGCCCCG | TTCTGGCGGC | AGGCGGGGGT | CGCCGACCGC | ATCGACCTTC GCATCGGCGA | 1740 |
| CGCCGCCCGG | ACCCTGTCCG | AGCTGCGTGC | ACACGAAGGC | GACGGCATCT TCGACCTGGT | 1800 |
| GTTCGTCGAC | | | | | 1810 |

(2) INFORMATION FOR SEQ ID NO:2:

(i) SEQUENCE CHARACTERISTICS:
  (A) LENGTH: 1810 base pairs
  (B) TYPE: nucleic acid
  (C) STRANDEDNESS: single
  (D) TOPOLOGY: unknown (xi) SEQUENCE DESCRIPTION: SEQ ID NO:2:

| | | | | | |
|---|---|---|---|---|---|
| GGATCCATCA | GATTCAAAGC | TGTCATCGTC | CCTGCCCTCC | TCTGAACTGC CGTCACCACA | 60 |
| GTGTCAACCG | GACACCGGTG | TCAGGAAAGG | AAAGCGGGCC | TGACTGTGTC ACCTCCGGGT | 120 |
| TGCCGGAGAA | ATACCCGGAA | ACCAGGATGG | GCGCGCCCGA | TCTCGGCCGA CGATTCGGCC | 180 |
| CCATTTCCAG | CGAAAGGAAC | AAGGATCG ATG GAG TCG CGC GTC GAG CGC CTA | 232 |

```
                                 Met Glu Ser Arg Val Glu Arg Leu
                                   1               5
```

| | | | | |
|---|---|---|---|---|
| CCT TCA CTG ACC GGG CTG CGC TGG TTC GCG GCG CTT TCC GTA TTC GTC | 280 |
| Pro Ser Leu Thr Gly Leu Arg Trp Phe Ala Ala Leu Ser Val Phe Val | |
|  10              15                  20 | |
| TGC CAT ATC GCC CAG CAG GGC ATT TTC GCC GAC CCG GAC GTG GCG TCC | 328 |
| Cys His Ile Ala Gln Gln Gly Ile Phe Ala Asp Pro Asp Val Ala Ser | |
|  25          30                  35                  40 | |
|  GCC CTG GGG CAC CTC ACG TCG CTC GGC TCG CTC GCG GTC TCC CTC TTC | 376 |
| Ala Leu Gly His Leu Thr Ser Leu Gly Ser Leu Ala Val Ser Leu Phe | |
|              45                  50                  55 | |
| TTC GTG CTG AGC GGC TAT GTG CTG ACG TGG TCG GCC CGG GAC GGC GAC | 424 |
| Phe Val Leu Ser Gly Tyr Val Leu Thr Trp Ser Ala Arg Asp Gly Asp | |
|                  60                  65                  70 | |
| TCC GTC AGA AGC TTC TGG CAG CGT AGG TTC GCC AAG ATC TAC CCG CTG | 472 |
| Ser Val Arg Ser Phe Trp Gln Arg Arg Phe Ala Lys Ile Tyr Pro Leu | |
|          75                  80                  85 | |
| CAT TTC GTC ACC TTC TGC ATT GCG GGC GTC ATC ATC TTC AGT CCT TCC | 520 |
| His Phe Val Thr Phe Cys Ile Ala Gly Val Ile Ile Phe Ser Leu Ser | |
|      90                  95                 100 | |
| GAG CCG GTG CTG CCG GGC GGT TCG ACG TGG GAC GGC ATG GTG CCC AAC | 568 |
| Glu Pro Val Leu Pro Gly Gly Ser Thr Trp Asp Gly Met Val Pro Asn | |

-continued

| | | | |
|---|---|---|---|
| 105 | 110 | 115 | 120 |

```
CTG CTG CTG GTG CAT TCA TGG CTG CCG GAC GCG TAC ATC GTC TCG GGA      616
Leu Leu Leu Val His Ser Trp Leu Pro Asp Ala Tyr Ile Val Ser Gly
            125             130             135

TTC AAC ACA CCG AGC TGG TCG CTT TCC TGT GAA ATG GCC TTC TAT CTC      664
Phe Asn Thr Pro Ser Trp Ser Leu Ser Cys Glu Met Ala Phe Tyr Leu
        140             145             150

ACG TTT CCG TTG TGG TAC CGG CTG CTG CTT CGG ATA CGG GTG AGC CGG      712
Thr Phe Pro Leu Trp Tyr Arg Leu Leu Leu Arg Ile Arg Val Ser Arg
        155             160             165

TTG TGG TGG TAC GCG GCC GCA CTG GCG CTG GCC GTG GTG TGC ATG CCG      760
Leu Trp Trp Tyr Ala Ala Ala Leu Ala Leu Ala Val Val Cys Met Pro
        170             175             180

TTC GTG GCC CGG CTG CTG CCG GAC AGC GCG GAG GTC GTT CCC GGG ATG      808
Phe Val Ala Arg Leu Leu Pro Asp Ser Ala Glu Val Val Pro Gly Met
185             190             195             200

CCG CTG CGG GAC ATG TGG TTC ACG TAC TGG TTC CCG CCC GTG CGG ATG      856
Pro Leu Arg Asp Met Trp Phe Thr Tyr Trp Phe Pro Pro Val Arg Met
                205             210             215

CTG GAG TTC CTC CTC GGC ATC GTG CTG GCG CTG ATC CGC CGC CAG GGG      904
Leu Glu Phe Leu Leu Gly Ile Val Leu Ala Leu Ile Arg Arg Gln Gly
        220             225             230

GCG TGG CGG GGG CCC GGA ACG GGC ACG GCC GCG CTG CTC CTC GGC GGC      952
Ala Trp Arg Gly Pro Gly Thr Gly Thr Ala Ala Leu Leu Leu Gly Gly
        235             240             245

GCG TTC GCG CTC AAC CAG GTG GTG CCG CCG ATG TTC ACC CTC ACC GCC     1000
Ala Phe Ala Leu Asn Gln Val Val Pro Pro Met Phe Thr Leu Thr Ala
250             255             260

ACC ACC GTC GTC CCC ATC GCC CTG CTG ATC GCC GCC GCG GCG GAC GGC     1048
Thr Thr Val Val Pro Ile Ala Leu Leu Ile Ala Ala Ala Ala Asp Gly
265             270             275             280

GAT CTG CGC GGG CGC CGT ACC GGA CTG CGC GCG GCC GTG CTG GTC AGG     1096
Asp Leu Arg Gly Arg Arg Thr Gly Leu Arg Ala Ala Val Leu Val Arg
        285             290             295

CTG GGC GAG TGG TCG TAC GCC TTC TAC CTG ATC CAC TTC CTG ATC ATT     1144
Leu Gly Glu Trp Ser Tyr Ala Phe Tyr Leu Ile His Phe Leu Ile Ile
            300             305             310

CGC TAC GGG CAC CGG CTG CTG GGC GGC GAC CAG GGA TAC GCC CGG CAG     1192
Arg Tyr Gly His Arg Leu Leu Gly Gly Asp Gln Gly Tyr Ala Arg Gln
        315             320             325

TGG GAC ACC CTC GCG GCG CTC GGC ATC ACA GCG GCG GTA CTG GGG GTC     1240
Trp Asp Thr Leu Ala Ala Leu Gly Ile Thr Ala Ala Val Leu Gly Val
330             335             340

ACG ATC GCC GCG AGC GCG GTC CTG CAC ATC TTC GTC GAG CGG CCC TGT     1288
Thr Ile Ala Ala Ser Ala Val Leu His Ile Phe Val Glu Arg Pro Cys
345             350             355             360

ATG ACC CTG CTG CGC GGC CGC CGC CCT CCG CAG GGG CCG GCT CCC GAC     1336
Met Thr Leu Leu Arg Gly Arg Arg Pro Pro Gln Gly Pro Ala Pro Asp
        365             370             375

TCC GGG GGC CGC CCG CAC CGG GCT CCG CTG GAA AGG GCA TGACGCGTGG      1385
Ser Gly Gly Arg Pro His Arg Ala Pro Leu Glu Arg Ala
        380             385

CCGACCAGAC CGTTCTCAGT CCGGCACTGC TGGAATACGC CAGGAGCGTC TCGCTGCGCG   1445

ACGACGCCGT GCTGCGCGAG CTGCGGGAGT TGACGGCGGC CCTGCCGGGC GGACGCGCCA   1505

TGCAGATCAT GCCGGAGGAG GCCCAGCTCC TCGCGCTGCT CATCCGGCTC ACGGGCGCCG   1565

CCCAGGTCCT GGAGATCGGC ACGTTCACCG GGTACAGCAC GCTGTGCATG GCCCGGGCAC   1625

TGCCGCCCGG CGGCCGGATC GTCACCTGCG ACATCACCGA GCGGTGGCCC GGCGTCGGC   1685

CCCCGTTCTG GCGGCAGGCG GGGGTCGCCG ACCGCATCGA CCTTCGCATC GGCGACGCCG   1745
```

```
CCCGGACCCT GTCCGAGCTG CGTGCACACG AAGGCGACGG CATCTTCGAC CTGGTGTTCG     1805
TCGAC                                                                1810
```

GENES ENCODING A 3-ACYLATION ENZYME FOR MACROLIDE ANTIBIOTICS

The present invention relates to DNA fragments containing a gene endowing host microorganism with an enzymatic activity for acylating the 3-position of macrolide antibiotics (this gene being referred to as "acyA"), to recombinant DNA plasmids containing such a DNA fragment, and to microorganisms transformed with such a recombinant plasmid, as well as to a method of producing 3-acylated macrolide antibiotics using such a transformed microorganism.

Macrolide antibiotics (14- or 16-membered cycles) are useful antibiotics widely used as a medicine and an animal medicine (for domestic animals or fishery). To cope with recent emergence of resistant bacteria of for some other reasons, various macrolide derivatives have been studied. It has been reported that acylation of the OH groups at the 3- and 4-positions of 16-membered cyclic macrolide antibiotics results in an increase in their antibiotic activities [cf. R. Okamoto, *Journal of Antibiotics*, 27, 524–544 (1979)]. According to this report, 3-acylated and 4"-acylated tylosin derivatives were synthesized and their activities on various bacteria having resistance to macrolide antibiotics were examined to reveal that 3-acylated and 4"-acylated tylosin, particularly 4"-acylated tylosin, have pharmacological effects on the resistant bacteria more potent than tylosin itself. However, tylosin-producing strains produce only tylosin derivatives which have —OH groups at the 3- and 4"-positions. In order to acylate such 3- and 4"-OH type tylosin, no method has been known other than chemical or biological methods.

The present invention provides an industrially useful method which makes it possible to convert bacterial strains which are unable to directly produce a 3-acylated product of macrolide antibiotics to one which can produce the 3-acylated macrolide using genetic engineering.

Examples of known macrolide antibiotics include the following.

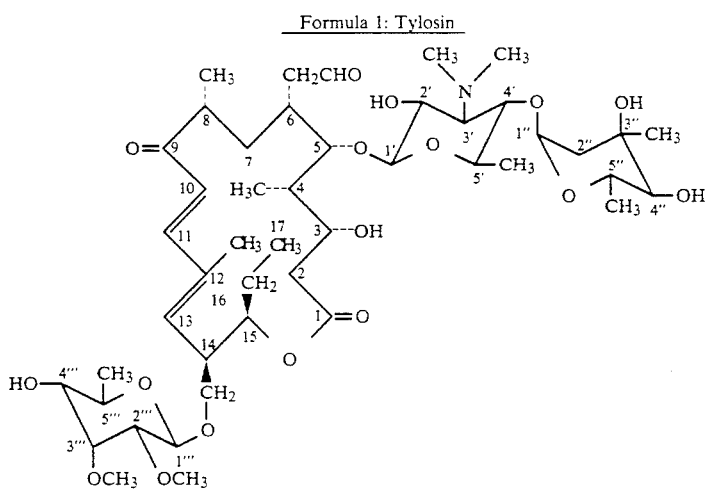

Formula 1: Tylosin

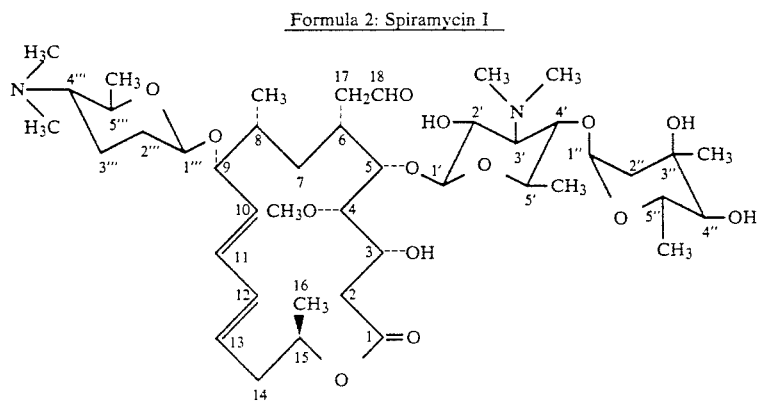

Formula 2: Spiramycin I

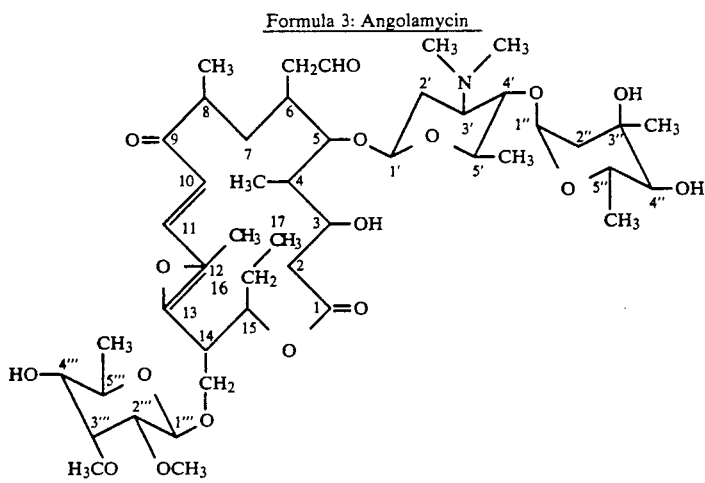

Formula 3: Angolamycin

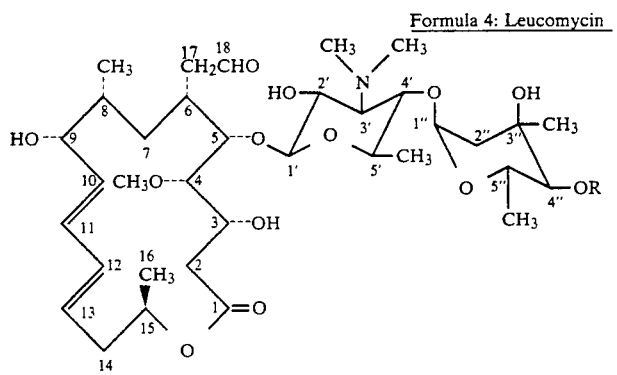

Formula 4: Leucomycin

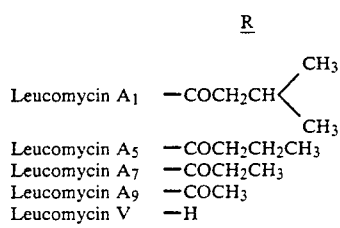

| | R |
|---|---|
| Leucomycin A$_1$ | —COCH$_2$CH(CH$_3$)$_2$ |
| Leucomycin A$_5$ | —COCH$_2$CH$_2$CH$_3$ |
| Leucomycin A$_7$ | —COCH$_2$CH$_3$ |
| Leucomycin A$_9$ | —COCH$_3$ |
| Leucomycin V | —H |

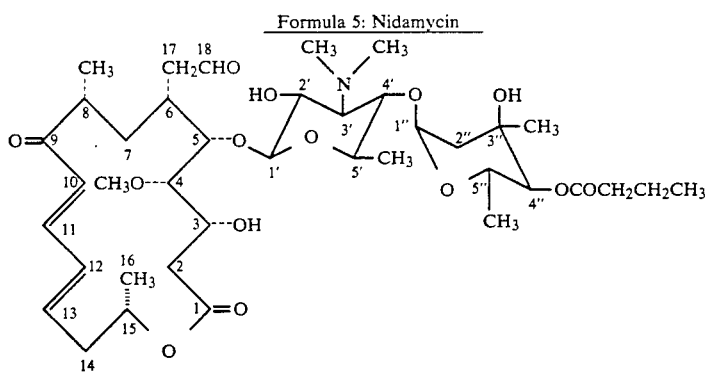

Formula 5: Nidamycin

While chemical methods have generally been used for acylating these antibiotics. [Omura et al., *Yakugaku Zasshi* (Bulletin of Pharmacy), 106, 729–757 (1986)], it has been difficult to efficiently acylate one or more specified positions in the molecule with the chemical methods. Accordingly, biological methods have been proposed (cf. U.S. Pat. No. 4,201,843.). Biological methods heretofore proposed include methods in which tyloin is acylated using microorganisms having the ability of acylating tylosin, culture media thereof or processed media, enzymes separated from the microorganisms, or contents of the microorganisms. For example, 3- and/or 4″-OH type macrolide antibiotics are added as a substrate to microorganisms cells such as *Streptomyces thermotolerans* ATCC 11416, *Streptomyces hygroscopicus* ATCC 21582, and *Streptomyces kitasatoensis* IFO 13686, culture media thereof or cell extracts therefrom for conversion reaction. However, this method involves different microorganisms, i.e., a macrolide antibiotics-producing bacterium and a microorganism having an acylation activity, which is uneconomical from a point of view of production on an industrial scale.

In order to biologically acylate 3- and/or 4″-OH type macrolideantibiotics, there have been necessary two steps of operations, i.e., at first incubation of a macrolide-producing strain which produces the macrolide concerned and isolation of the macrolide antibiotics therefrom, and then conversion of the compound with a microorganism having an acylation enzyme. Accordingly, with view to improving the conventional method and producing acylated macrolides with macrolide-producing strains alone, the present inventors have attempted to isolate genes for macrolide acylation enzymes from microorganisms having the genes and introduce the genes into macrolide-producing strains by genetic engineering techniques to have the acylated macrolides by the genetically engineered strains directly. Among the genes for the acylation enzymes, gene encoding a 4"-acylation enzyme (acyB) has already been isolated and recently reported in, for example EP-A-345,546. However, no enzyme encoding a 3-acylation enzyme has been cloned yet. Accordingly, the present inventors have tried to isolate a 3-acylation enzyme coding gene (acyA) in order to achieve the above-described object.

Recent development in genetic engineering techniques has made it possible to isolate a desired gene from a specified organism and introduce it as-is, or after ligating it to a suitable vector, into another desired organism (D.A. Hopwood et al., *Genetic Manipulation of Streptomyces*. The John Innes Foundation (1985)).

Accordingly, the present inventors have made intensive investigation with view to isolating a gene encoding a 3- and/or 4"-acylation enzyme for acylating 3- and/or 4"-position of a macrolide antibiotics as described above from a microorganism having such an enzyme. As a result, the present inventors have been successful in isolating a 3-acylation enzyme-coding gene (acyA) from a certain strain belonging to the genus of Streptomyces, thus completing the present invention.

Therefore, according to the present invention, there is provided a DNA fragment or a restriction enzyme-digested DNA fragment, the DNA fragment containing a gene, acyA, encoding a 3-acylation enzyme for macrolide antibiotics, characterized by being derived from a strain belonging to the genus Streptomyces, having a size of about 1.8 kb, and having a DNA base sequence shown in a restriction enzyme map shown in FIG. 1 (A) in the attached drawing.

Also, according to the present invention, there is provided a DNA fragment or a restriction enzyme-digested DNA fragment, the DNA fragment containing a gene, acyA, encoding a 3-acylation enzyme for macrolide antibiotics, characterized by being derived from a strain belonging to the genus Streptomyces, having a size of about 3.2 kb, and having a DNA base sequence shown in a restriction enzyme map shown in FIG. 1 (B) in the attached drawing.

Here, by the term "restriction enzyme-digested DNA fragment" is meant various sizes of DNA fragments obtained by digestion with a restriction enzyme to lengths necessary for expressing an acylation enzyme activity.

The DNA fragment or digested DNA fragment containing the gene acyA of the present invention is useful for commercially producing the objective macrolide antibiotics derivatives, for example, 3-acylated tylosin, and is particularly useful in that it enables commercial utilization of recombinant DNA technology for antibiotics-producing microorganisms such as Streptomyces and other genera.

FIGS. 1 to 12 attached hereto will be explained briefly as follows.

FIGS. 1 (A) and FIG. 1 (B) are each a restriction enzyme map of a DNA fragment containing the gene acyA of the present invention;

FIG. 6 is a base sequence of acyA, which base sequence is identified in the attached Sequence Listing as SEQ ID No. 1;

FIG. 7 is an amino acid sequence corresponding to the base sequence of acyA, which amino acid sequence is identified in the attached Sequence Listing as SEQ ID No. 2;

FIG. 13 is a restriction enzyme cleavage site and function map of plasmid pY-17ΔEco depicting the HindIII cleavage site.

FIG. 14 is a restriction enzyme cleavage site and function map of plasmid pMAB1 depicting the XbaI cleavage site.

Figure 2:
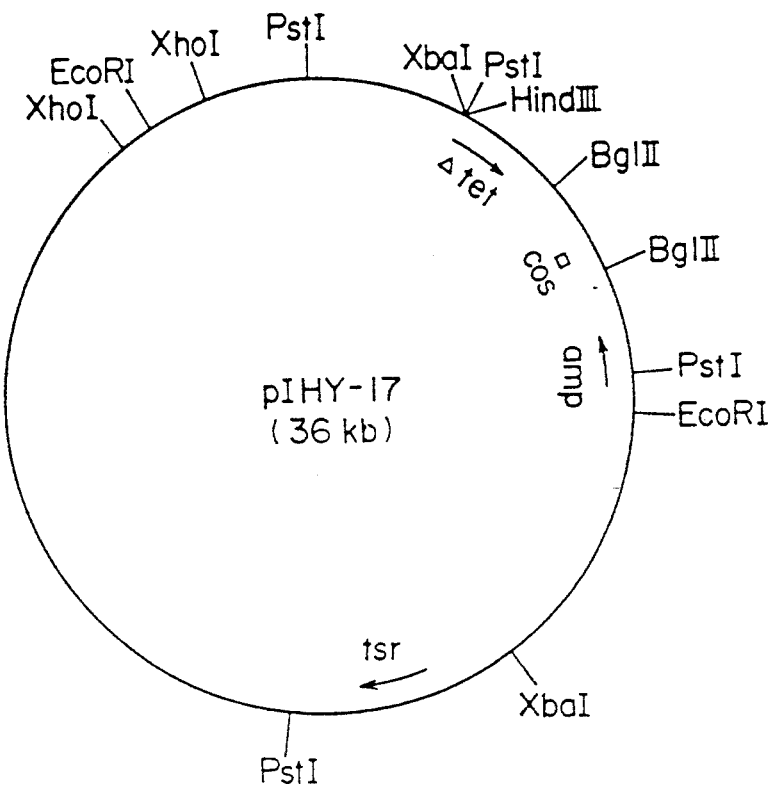
FIG. 2 is a restriction enzyme cleavage site and function map of plasmid pIHY-17.

Hereafter, a more detailed explanation will be given on production of DNA fragments containing the gene acyA of the present invention, and characteristics thereof as well as production of acylated macrolide antibiotics using transformed microorganisms obtained using the DNA fragments.

As for the strain belonging to the genus Streptomyces which is a source from which the DNA fragment containing the gene acyA of the present invention is derived may be any strain that has an ability for producing a 3-acylation enzyme for macrolide antibiotics. Examples of such a strain include *Streptomyces ambofaciens, Streptomyces kitasatoensis, Streptomyces narbonensis* var *josamyceticus, Streptomyces hygroscopicus, Streptomyces platensis, Streptomyces albireticuli, Streptomyces cinerochromogenes, Streptomyces djakartensis, Streptomyces furdicidicus, Streptomyces macrosporeus, Streptomyces tendae, Streptomyces thermotolerans,* and *Streptomyces deltae*. Among them, preferred is *Streptomyces thermotolerans*.

While explanation will be made hereinafter on the case where the preferred *Streptomyces thermotolerans* is used, the gene acyA encoding an enzyme for acylating the 3-position of macrolide antibiotics can be isolated similarly also in the case where other strains are used.

Preparation of Genome

*Streptomyces thermotolerans,* a donor of the DNA fragment containing the gene acyA of the present invention has been deposited, e.g., at The American Type Culture Collection under deposition number ATCC 11416, and is available without difficulty.

This strain is incubated at 28° C. aerobically to obtain bacterial cells at a logarithmic growth phase, and processed by the method of Hopwood et al. [Genetic Manipulation of Streptomyces: A laboratory Manual, John Innes Foundation, Norwich, United Kingdom (1985)]

to prepare an acyA-containing genome DNA, as will be described in greater detail in Example 1 described hereinbelow.

Cloning of *S. thermotolerans* Carbomycin Biosynthesis Related Gene Region

It has been reported that generally, all or most of the genes relating the biosynthesis of antibiotics by bacteria belonging to the genus Streptomyces are present in cluster in a specific region on a genome DNA or on a plasmid DNA [cf., e.g., Fishmann et al., *Proc. Natl. Acad. Sci. USA,* 84, 8248 (1987); Binnie et al, *Journal of Bacteriology,* 171, 887 (1989)]. The gene acyA of the present invention encodes an enzyme acylating the hydroxyl group at the 3-position of carbomycin, one of macrolide antibiotics, produced by *S. theremotolerans* and hence it can be considered as one of the genes relating to the biosynthesis of that antibiotics and therefore it is presumed that the gene acyA forms a cluster with other genes relating to the biosynthesis. Accordingly, in order to obtain the gene acyA of the present invention from the genome DNA of *S. thermotolerans,* it is desirable to at first clone the carbomycin biosynthesis-related gene region using a cosmid vector or the like. This is because when the clone thus obtained is used as a sample for isolating acyA in a limited region, it is much more efficient cloning means than the use of the entire genome DNA as a sample. More specifically, for example; Partially-digested Sau 3AI fragments of genome DNA of *S. thermotolerans* are inserted in BamHI site of a cosmid vector pHC79 of *E. coli* and packaged in vitro in λ-phage to prepare a gene library of *S. thermotolerans*. The preparation of gene library utilizing such a cosmid can be carried out using general genetic engineering techniques frequently used on various organisms for the purpose of isolating a specific gene (cf., e.g., Maniatis et al., *Molecular Cloning,* 295-307, Cold Spring Harbor Laboratory).

Further, the procurement of the clone containing the carbomycin biosynthesis-related gene region from the gene library can be achieved by preparing a probe from a gene known to belong to the carbomycin biosynthesis-related gene region or DNA fragment near the gene, and performing colony hybridization of the probe with a gene library prepared using *E. coli* HB101 as a host (i.e., many clones obtained by transduction of packaged cosmid DNA having the genome DNA fragment of *S. thermotolerans*). By this operation, there can be obtained clones hybridizing with the probe, i.e., clones having cosmids containing the carbomycin biosynthesis-related gene region. The cosmids derived from these clones have inserted fragments of up to about 45 kb containing as a probe a part or all of the DNA fragment and extending to neighboring regions. For example, one of the recombinant cosmids above celled "pSE26" by the present inventors has an inserted fragment of about 45 kb containing an acyB fragment near a terminal on one side of the insert portion (cf. Example 2, C below).

Since the length of DNA fragments which can be inserted in cosmids has an upper limit, screening using a single kind of probe does not always result in inclusion of whole of the biosynthesis-related gene region in the inserted fragment. One method for solving this problem is, for example, to isolate a new DNA fragment of a suitable size from a region which is as remote as possible from the probe region in the inserted pSE26 fragment, and use the fragment as a probe. Using the probe, colony hybridization from the *S. thermotolerans* library can be performed again to obtain cosmids from clones which have hybridized. As described above, recombinant cosmids can be isolated which have a region partially overlapping pSE26 and a region which is considerably remote from the acyB-containing DNA fragment used as the first probe as an inserted fragment, for example, pBM73 shown in Example 2, C, below. In this manner, and repeating this procedure, it desired, cloned region can be expanded and consequently all of the carbomycin biosynthesis-related genes can be cloned from the gene library of *S. thermotolerans.*

As described above, the cloning of a region containing the objective gene within the range of several tens kb to several hundreds kb by preparing, from a clone obtained by hybridization with a probe, a new probe in a region remote from the original probe followed by obtaining a clone which hybridizes with the new probe or repeating this procedure several times as the case may be, can be carried out using a method generally known to one skilled in the art as "gene walking" [cf. e.g., Tashiro et al., Zoku Seikagaku Jikken Koza (Second Series: Corse of Biochemical Experiments), Vol. 1, Idenshi Kenkyusho (Methods of Gene Study) II, 83-104 (1986), ed. by Japan Biochemistry Society).

Cloning of acyA gene Using Vector Plasmid pIHY-17

Shuttle cosmid pIHY-17 can be constructed as a vector for cloning and expressing the gene acyA of the present invention (cf. FIG. 2). This vector is a vector which has both functions of Actinomyces vector pIJ922 and *E. coli* cosmid pHC79 simultaneously, and is constructed concretely by the method described in Example 3 below. Generally, vectors having advantages that they can be introduced and propagated in both of *E. coli* and *Actinomyces,* i.e., shuttle vectors can be constructed with ease by connecting an *E. coli* vector to an *Actinomyces* vector. In order to have the instant vector pIHY-17 similar advantages, respective replicons of *Actinomyces* vector pIJ922 and *E. coli* vector pHC79 are incorporated and respective selective markers are given. In addition, the instant vector is endowed with packaging function derived from the cos site of pHC79.

This function makes it possible to introduce even a large plasmid having a length of up to about 50 kb inclusive of the length of the vector into *E. coli* as a host through in vitro packaging of λ-phage with ease. The above-described function of pIHY-17 as a shuttle cosmid is suitable for efficient closing and expression of acyA. For example, cloned fragment derived from the carbomycin biosynthesis-related gene region can be ligated with the instant vector and packaged in vitro in λ-phage making the use of the cos site thereof. A number of clones obtained by the transduction of the reconstructed cosmids into *E. coli* HB101 are mixed and the cosmids can be extracted. The pooled cosmids can be transformed into *Actinomyces, S. lividans* and the like making the use of the function which pIJ922 has. From the transformants thus obtained, strains to which the gene acyA of the invention has been donated, that is strains having an activity of acylating the 3-position of macrolides, can be selected by thin layer chromatography tests, resulting in that acyA is cloned.

Unlike the case where vectors for the exclusive use of Actinomyces, the above-described method can provide in the *S. lividans* transformation DNA's securely cyclized and amplified by the operations of in vitro packaging and transduction.

Strains having the activity of the gene acyA of the invention, for example, *S. lividans* 53A strain, can be separated by the above-described method. Also, by treating the strains as described in Example 4 below, plasmids, for example, p53A, can be isolated. Whether or not the gene acyA of the invention is present in the inserted fragment of the plasmid can be made clear by examining a strain obtained by retransformation of *S. lividans* with the plasmid to see if the retransformed strain has an activity of acylating the 3-position of macrolides. The inserted fragment can be cut out of the original plasmid utilizing suitable restriction sites, and then subcloned in *E. coli* vector pUC19 or the like. Plasmids thus obtained, for example, pMAA2 and pMAA3 (cf. FIG. 4) can be prepared rapidly and easily in large amounts and hence they can be used as a material suitable for the analysis of the structure and expression function of the gene acyA of the invention.

Utility of Restricted DNA Fragment Containing Gene acyA

3-Acylation enzyme for macrolide antibiotics expressed using the gene acyA of the invention is useful for the acylation of the 3-position of, particularly, tylosin but its utility is not limited thereto and has also a 3-acylation ability for other macrolide antibiotics such as spiramycin, angolamycin, leucomycin and nidamycin.

Therefore, the introduction of plasmids having incorporated therein the gene acyA of the invention into microorganisms having an ability of producing these macrolide antibiotics enables direct production of 3-acylated macrolide antibiotics by the microorganisms.

Also, it is possible to introduce such recombinant plasmids into microorganisms producing no macrolide antibiotics, and cultivation of such transformed strains in a medium containing a macrolide antibiotics can result in biosynthesis of 3-acylated macrolide antibiotics.

Further, the 3-acylated enzyme produced by the transformed strains can of course be used as a catalyst in an enzymatic reaction between macrolide antibiotics and acylating agents.

In addition, when used together with a 4"-acylation enzyme-coding gene (referred to as "acyB") which has already been isolated and disclosed in EP-A-345,546, the gene acyA facilitates the production of 3-O-acetyl-4"-O-isovaleryltylosin, an industrially useful acylation derivative of tylosin, by fermentation.

As described above, DNA fragments containing the gene (acyA) encoding 3-acylation enzyme for macrolide antibiotics provided by the present invention has a wide utility.

Transformation of Microorganisms With Plasmids Having Incorporated Therein Restricted DNA Fragment Containing Gene acyA Plasmids having incorporated therein the gene acyA of the invention can be introduced into suitable host microorganisms depending on the vector plasmid used. The host microorganisms may be either those having an ability of producing macrolide antibiotics or those having no such ability. Examples of the host microorganism which can be used include *Streptomyces kitasatoensis*, *Streptomyces narbonensis* var *josamyceticus*, *Streptomyces hygroscopicus*, *Streptomyces platensis*, *Streptomyces albireticuli*, *Streptomyces cinerochromogenes*, *Streptomyces djakartensis*, *Streptomyces macrosporeus*, *Streptomyces tendae*, *Streptomyces deltae*, *Streptomyces fradiae*, *Streptomyces eurythermus*, *Streptomyces ambofaciens*, *Streptomyces kasugaensis*, *Streptomyces erythreus*, *Streptomyces kanamyceticus*.

However, generally macrolide antibiotics-producing bacteria which produce substantially no 3-acylation enzyme for macrolide antibiotics, for example, *Streptomyces eurythermus* ATCC 14975 which is an angolamycin-producing strain, and *Streptomyces fradiae* ATCC 19609 which is a tylosin-producing strain are suitable.

The transformation of the host microorganisms with the recombinant plasmids containing the gene acyA can be performed by a method known per se, e.g., the method of Hopwood (cf. Genetic Manipulation of Streptomyces: A Laboratory Manual (1985), The John Innes Institute).

The cultivation of the transformed microorganisms thus obtained in media containing macrolide antibiotics enables production of 3-acylated macrolide antibiotics. Alternatively, 3-acylated macrolide antibiotics can be produced by cultivating the transformed microorganisms even in media containing no macrolide antibiotics when the transformed microorganisms used have an ability for producing macrolide antiiotics.

Further, 3-acylated macrolide antibiotics can also be produced by cultivating the transformed microorganisms, and reacting macrolide antibiotics with an acylating agent such as acetyl coenzyme A, propionyl coenzyme A, or a precursor of biosynthesis of an acyl group-donor, e.g., leucine, in the presence of the cultivated bacterial cells themselves or their processed products (for example, cell-free extracts obtained by supersonication of cultivated cells).

Thus, according to the present invention, macrolide antibiotics of which the 3-position is acylated with an alkanoyl group having 1 to 3 carbon atoms, for example, an acetyl group, a propionyl group, etc., such as 3-O-acetyl tylosin, 3-O-propionyltylosin, 3-O-acetylangolamycin, 3-O-propionylangolamycin, 3-O-acetylspiramycin, and 3-O-propionylspiramycin, can be produced.

Also, macrolide antibiotics of which the 3- and 4"-positions are acylated simultaneously, such as 3-O-acetyl-4"-isovaleryltylosin, 3-O-acetyl-4"-n-butyryltylosin, 3-O-acetyl-4"-O-propionyltylosin, 3-O-acetyl-4"-O-acetyltylosin, and 3-O-propionyl-4"-O-isovaleryltylosin, can be produced by using plasmids having in corporated therein acyA and 4"-acylating enzyme coding gene (acyB) as described above, or by using different plasmid having incorporated therein acyB together with the above-described plasmid having incorporated therein acyA.

Cultivation of Transformed Strains

The host microorganisms transformed with the plasmid containing the DNA fragment containing the gene acyA of the invention, for example, microorganisms belonging to the genus Streptomyces, can be cultivated by many methods using any media of different types. Preferred examples of carbon source which can be added to the culture media include molasses, glucose, starch, oils, fats, glycerin and the like. Examples of the nitrogen source include soybean powder, amino acid mixtures, dry yeast, peptones, and the like. The media may contain nutrient inorganic salts, which contain usually used salts that can release potassium, sodium, magnesium, calcium, phosphoric acid, chlorine and sulfuric ions. Indispensable minor components, for example, vitamins may be added to the media, if desired. The minor components may be supplied in the form of impurities accompanying other components of the culture media. Further, the media may contain macrolide antibiotics to be acylated, if desired.

The transformed microorganism belonging to the genus Streptomyces can be cultivated under aerobic conditions in media over a relatively wide pH range of pH within the range of pH about 5 to 9 and within the temperature range of about 20° to 40° C. On this occasion, a condition necessary for maintaining the stability of plasmids, for example a chemical such as thiostreptone, may be added to the media as a selection pressure.

Hereafter, the present invention will be explained in more detail by way of examples. However, these examples are examplary and by no means limit the scope of the present invention.

EXAMPLE 1

Preparation of Genome DNA of *Streptomyces thermotolerans* ATCC 11416

(A) Cultivation of *Streptomyces thermotolerans* ATCC 11416

In a slant medium containing 0.4% of glucose, 0.4% of yeast extract, 1.0% of malt extract, and 1.5% of agar was cultivated the aforementioned strain at 29° C. for 2 weeks, and one platinum loopful of the strain was taken out and inoculated in 25 ml of a seed medium containing 2% of soluble starch, 2% of soybean powder. 0.1% of yeast extract, 0.1% of $K_2HPO_4$, and 0.05% of $MgSO_4.7H_2O$. As the seed medium was used one which had been placed in a 250 ml Erlenmeyer flask and sterilized at 120° C. for 15 minutes. The inoculated flask was incubated by shaking culture at 28° C. for 48 hours to obtain a seed. One (1) ml of the seed was inoculated in 25 ml of a TSB medium (trypticase soy broth medium)* and thereafter the medium was incubated at 28° C. for 48 hours.

*TSB medium was prepared to a concentration of 30 g/liter.

TSB medium was available from BBL Microbiology Systems Maryland, United States of America.

(B) Preparation of Genome DNA

Mycelia were collected and washed once with a 10.3% sucrose solution. Subsequently, 25% sucrose/Tris-HCl (50 mM, pH 8) was added to the mycelia in an amount of 5 ml per g of wet cell. After well dispersing the mycelia, 0.6 ml of lysozyme (Grade I prepared by Sigma Chemical Co.) solution (10 mg/ml) was added to the mixture and well mixed. After incubating at 30° C. for 30 minutes and adding 0.6 ml of EDTA solution (0.5M, pH 8) and 0.1 ml of pronase E (prepared by Sigma Chemical Co.) solution (10 mg/ml) thereto, the mixture was incubated at 30° C. for 5 minutes. 6 ml of a phenol layer obtained by mixing 500 g of phenol and 500 g of chloroform with 200 ml of Tris-HCl (50 mM, pH 8)/NaCl (100 mM)/EDTA (5 mM, pH 8) was added to the mixture and well mixed under mild conditions. Then, the solution was fractionated by centrifugation (10,000 rpm, 10 minutes) to obtain about 7 ml of an aqueous layer. After adding 2 ml of chloroform to the aqueous layer and well mixing under mild conditions, the mixture was centrifuged (10,000 rpm, 10 minutes) to obtain about 7 ml of an aqueous layer. To the aqueous layer was added 30 µl of ribonuclease A type I-AS prepared by Sigma Chemical Co.) solution (10 mg/ml solution heated at 90° C. for 10 minutes), and the mixture was incubated at 37° C. for 1 hour. After adding 0.1 volume of an aqueous sodium acetate solution (3M, pH 4.8) and 1 volume of isopropanol thereto and well mixing, the resulting mixture was left to stand at room temperature for 10 minutes. The precipitation which formed were collected by centrifugal separation (6,000 rpm, 10 minutes). After dissolving the precipitates in 5 ml of TE buffer [Tris-HCl (10 mM, pH 8)/EDTA (1 mM, pH 8), 0.5 ml of an aqueous sodium acetate solution and 12.1 ml of ethanol were added and well mixed, and the resulting mixture was left to stand at −20° C. overnight. The precipitates which formed were collected by centrifugation (6,000 rpm, 10 minutes), and dried in a dessicator under vacuum. Thus, about 800 µg of genome DNA was obtained from 25 ml of the culture medium.

EXAMPLE 2

Cloning of Carbomycin Biosynthesis-Related Gene Region (A) Preparation of Cosmid Vector pHC79

A single colony of *E. Coli* HB101 transformed with pHC79 (Boehringer Mannheim) (Transformation Kit, produced by Nippon Gene Co., Ltd.) was inoculated in 2 ml of L-broth (1% bactotryptone, 0.5% yeast extract, 0.5% NaCl, pH 7.4) containing ampicillin in a final concentration of 50 mg/ml, and cultivated by shaking culture at 37° C. overnight. The culture medium was added to 500 ml of ampicillin (50 µg/ml)-added L-broth, and cultivated again by shaking culture at 37° C. overnight. After the cultivation, the medium was centrifuged at 5,000 rpm, at 4° C. for 10 minutes. The resulting pellet was suspended in 20 ml of a solution A composed of 25 mM Tris-HCl, pH 8, 10 mM EDTA, and 60 mM glucose, on ice. Then, a solution of 40 mg of lysozyme (Seikagaku Kogyo Co., Ltd.) dissolved in 0.5 ml of water was added thereto, and mixed mildly. The resulting mixture was left to stand at room temperature, and when cells initiated to be lysed (usually, 2 to 5 minutes after the mixing), 40 ml of fresh solution B (1% SDS, 0.2N NaOH) which had been prepared in advance and cooled was added quickly and mixed mildly, and the resulting mixture was left to stand for 5 minutes on ice. Thereafter, 30 ml of a cooled solution C (29.3% potassium acetate, 11.5% acetic acid) was added thereto, and the mixture was shaken vigorously and then left to stand on ice for 5 minutes. This was centrifuged at 8,000 at 4° C. for 10 minutes to obtain about 90 ml of a supernatant, to which was added 0.6 volume of isopropanol. The mixture thus obtained was left to stand at room temperature for 10 minutes, and then centrifuged again at 8,000 rpm at 15° C. for 10 minutes to obtain precipitates. After washing the precipitates once with 50 ml of 70% ethanol the precipitates were dried well at room temperature under reduced pressure. The precipitates thus dried were dissolved in 8.2 ml of TE (10 mM Tris-HCl, pH 8, 1 mM EDTA) and 8.4 g of cesium chloride and 0.2 ml of a 10 mg/ml ethidium bromide solution were added thereto sequentially. The solution obtained were poured into two centrifugation tubes "quick seal" (Beckmann Co.), and centrifuged at 65,000 rpm for 4 hours, or at 5,000 rpm for 15 hours, using a vTi65 rotor. Thereafter, a band containing plasmids which appeared in the tube was recovered in a 5 ml syringe (Thermo). The solution was extracted with equivalent volume of n-butanol 3 to 4 times to remove ethidium bromide, and have plasmid DNA precipitated with 3 times the volume of 70% ethanol, and further the pellet was washed 3 times with 70% ethanol. The pellet thus washed was finally dissolved 0.5 to 1 ml of TE buffer. By this method, 300 µg of pHC79 plasmid DNA was obtained from 500 ml of L-broth.

(B) Preparation of *S. thermotolerans* Gene Library.

The preparation of such a library using pHC79 was carried out substantially according to the method taught by Ishi-Horowicz, Burke, *Nucleic Acids Research*, vol. 9, 2987 (1981). That is, two aliquots (50 µg each) of pHC79 were linearized one with HindIII and the other with SalI, and dephosphorylated with calf intestine-derived alkaline phosphatase (Boehringer Mannheim Yamanouchi Co., Ltd.). Then the both DNA's were digested with BamHI to form arms on both sides which were able to be ligated at only one terminal thereof. The both side arms (1.5 µg each) and 4 µg of a partial digest of the genome DNA of *S. thermotolerans* with Sau 3AI (decomposate obtained by digesting 50 µg of genome DNA of *S. thermotolerans* with Sau 3AI4µ in 200 µl of Sau 3AI buffer at 37° C. for 2 minutes) were combined to make 12 µl, and 0.5 µl (300 µ) of T$_4$ DNA ligase (Nippon Gene) was added thereto, followed by ligation at 16° C. overnight. After the reaction, DNA was concentrated by precipitation with ethanol, and a portion (equivalent to 4.6 µg) thereof was subjected to in vitro packaging using an in vitro packaging kit, Gigapack Gold (Stratagene) according to the protocol attached to the kit. Further, transduction into *E. coli* MB101 was conducted under the conditions described in the protocol. Upon examination, the titer was $2.8 \times 10^5$ colony forming unit (cfu).

(C) Procurement of Cosmid Having Carbomycin Biosynthesis-Related Gene Region

About 19,000 colonies of the above-described gene library were subjected to colony hybridization according to the method described in *Basic Methods in Molecular Biology*, p. 227-229 (1986), Elsevier Science Publishing Co., Inc., 523 Vanderbilt Avenue, New York, N.Y. 10017, U.S.A. As the probe was used a portion of DNA fragment containing a macrolide 4″-acylation enzyme-coding gene (acyB) nick-translated with [α-32P]dCTP (Amersham Japan Co., Ltd.), more specifically 1 kb EcoRI-SacI fragment of plasmid pY-17ΔEco described in EP-A-345,546. For detailed explanation on the nick translation, reference is made to Maniatis, Fritsch and Sambrook, Molecular Cloning, Cold Spring Harbor Laboratory, Box 100, Cold Spring Harbor, N.Y., p. 109-112. As a result, 19 cosmid clones containing the carbomycin biosynthesis-related gene region which have hybridized with the probe were procured. For the purpose of extending the cloned region, the strain SE26 was selected among the clones and plasmid pSE26 was separated therefrom by the method described in item (A) in this Example. Using 1.0 kb BamHI-restricted fragment of this cosmid as a probe, screening from the library was repeated again, and as a result about 20 strains of positive clones including BM73 containing cosmid pBM73 were obtained.

EXAMPLE 3

(A) Preparation of pIJ922

Spores ($10^8$ cells) of *Streptomyces lividans* TK64/PIJ922 (obtained from the John Innes Streptomyces Culture Collection, John Innes Institute, Colney Lane, Norwich NR4 7UH, England) were inoculated in 500 ml of YEME+34% suclose medium (0.3% yeast extract, 0.5% bactopeptone, 0.3% malt extract, 1% glucose, 34% sucrose, and after sterilization 1 ml of 2.5M MgCl$_2$ solution was added thereto) containing 5 µg/ml of thiopeptine*, cultivated by shaking culture at 28° C. for 48 hours.

*Thiopeptine (prepared by extracting Thiofeed produced by Fujisawa Pharmaceutical Industry Co., Ltd. with chloroform) was used as a selection pressure instead of thiostreptone (cf. S. Pastka and J. W. Boldley, *Antibiotic III*, 5, p. 1-573 (1975) Springer-Verlag).

The mycelia were collected and washed once with a 10.3% suclose solution. Then, the mycelia were suspended in 45 ml of a 10.3% sucrose/Tris-HCl (25 mM, pH 8)/EDTA (21 mM, pH 8) solution. After adding 5 ml of a lysozyme solution (10 mg/ml, dissolved in the same solution as used for suspending the mycelia) and 250 µl of a ribonuclease type I-AS solution to the cell suspension and mixing it well, the suspension was incubated at 37° C. for 30 minutes. Subsequently, 30 ml of a 0.3M NaOH/2% SDS solution was added thereto and well mixed therewith, followed by incubation at 55° C. for 15 minutes. The same phenol solution as used in Example 1 (B) (20 ml) was added to the suspension and well mixed therewith. The suspension was centrifuged (15,000 rpm, 15 minutes) to separate into layers, and about 70 ml of an aqueous layer was obtained. To the aqueous layer were added 7 ml of a sodium acetate solution (3M, pH unadjusted) and 70 ml of isopropanol, and after well mixing the mixture was left to stand at room temperature for 10 minutes. After centrifugation (15,000 rpm, 15 minutes, precipitates were collected, and dissolved in 10 ml of a TNE buffer [Tris-HCl (10 mM, pH 8)/EDTA (1 mM, pH 8)/NaCl (50 mM). Thereafter, 5 ml of the above-described phenol solution was added to the solution and the mixture was mixed well.

Next, the mixture was centrifuged (15,000 rpm, 15 minutes) to separate into layers, and about 10 ml of an upper layer was obtained. The upper layer was mixed with 1 ml of a sodium acetate solution (3M, pH 6) and 10 ml of isopropanol and mixed well. After centrifugation (15,000 rpm, 15 minutes), precipitates were collected and washed with 1 ml of ethanol and dried. After dissolving the precipitates in 11.9 ml of TE buffer, 12.6 g of cesium chloride, and then 0.6 ml of an ethidium bromide solution (10 mg/ml) were added thereto. The mixture was centrifuged at 36,000 rpm for 60 hours, and the fraction containing a plasmid band was extracted with TE buffer and ispropanol saturated with cesium chloride 5 times to remove ethidium bromide. Thereafter, the fraction was charged in a tube for dialysis and dialyzed against TE buffer for 24 hours. Thus, about 50 µg of plasmid pIJ922 were obtained.

(B) Procedure of Construction of pIHY-17

*E. coli* cosmid pHC79 (2 µg) prepared as in Example 2 was digested with EcoRI and HindIII, extracted, purified and dissolved in 20 µl of TE buffer. On the other hand, after digesting 50 µg of pY-17ΔEco (cf. EP-A-345,546) with EcoRI and HindIII, the decomposate was subjected to electrophoresis in TAE buffer/0.8% ararose gel (40 mM Tris-HCl, 20 mM sodium acetate, 1 mM EDTA, (adjusted to pH with acetic acid), 0.8% agarose) at 6 v/cm. After 4 hours, electrophoretogram was stained with ethidium bromide and then about 6 kb band was cut off on a transilluminator and 6 kg fragment in the gel piece was extracted and purified using GENE CLEAN KIT (Bio101) according to the protocol attached thereto.

The fragment (0.6 μg) and the aforementioned EcoRI-HindIII-decomposate of pHC79 [0.2 μg (2 μl)] were incubated in 20 μl of a T4DNA ligase (Nippon Gene) solution (300 units/20 μl) at 16° C. overnight. The reaction mixture (5 μl ) was added to 150 μl of *E. coli* HB101 competent cell to perform transformation.

As for detailed information on transformation, reference is made to Davis, et al., Basic Methods in Molecular Biology, p. 70–90.

From 6 strains among the resulting transformed strains (ampicillin resistants) were extracted plasmids on a small scale, and the plasmids were inspected to see if a 6 kb fragment is present by examining electrophoresis patterns of their EcoRI-HindIII decomposates. As a result, three strains had the objective 6 kb fragment. A plasmid was prepared by the method described in Example 2 (A) from one of the three strains.

The plasmid thus obtained (5 μg) was made linear with EcoRI, and dephosphorylated with calf intestine-derived alkaline phosphatase (Boehringer Mannheim). The resulting DNA (1.25 μg) and EcoRI-linearized DNA of pIJ922 (4 μg) wre reacted in 7 μl of a T4DNA ligase (Nippon Gene) solution (200 units/7 μl) at 16° C. for 4 hours. The reaction mixture (4 μl) was subjected to in vitro packaging using Gigapack Gold (Stratagene), followed by transduction into *E. coli* HB101.

From the thus-obtained HB101 transduced strains were selected 6 strains, and plasmids were inspected to reveal that 4 strains among the 6 strains had the objective plasmid pIHY-17 (cf. FIG. 2). A plasmid was prepared from one of the 4 strains on a large scale in the same manner as in the method described in Example 2 (A), and as a result 1.65 mg of plasmid DNA was obtained from 1 l of L-broth.

EXAMPLE 4

Procurement of p53A (A) Incorporation of Carbomycin Biosynthesis-Related Gene Region DNA Fragment pIHY-17 prepared in Example 3 above was divided into two portions each in an amount of 25 μg, and one was digested with HindIII and the other with EcoRI, followed by dephosphorylation with alkaline phosphatase.

Then, these were cut with XhoI, and each decomposate was subjected to electrophoresis on TAE/0.6% agarose. From the electrophoretogram were separated and purified 30 kb HindII-XhoI fragment and 11 kb EcoRI-XhoI fragment [GENE CLEAN KIT (BI-O101)]. Each fragment (1 μg), XhoI-complete decomposate (1 μg) of and SalI-imcomplete decomposate (2 μg) of cosmid clone mixture (pSE26 and pBM73, etc.) containing the carbomycin biosynthesis gene region prepared by the method descried in Example 2 were mixed and incubated in 25 μl of a T4DNA ligase (Nippon Gene) solution (750 units/25 μl) at 16° C. overnight.

After completion of the reaction, DNA was precipitated, and dissolved again in 5 μl of TE buffer. The reaction mixture (2.5 μl) was subjected to in vitro packaging [Gigapack Gold Kit (Stratagene)]. Followed by transduction into *E. coli* HB101. As a result about 2,500 strains of the resulting *E. coli* clones on a plate were collected by suspending them in 10 ml of L-broth, and pooled plasmids were extracted by practicing the method described in Example 2 on a small scale to obtain 20 μl of TE solution, which was used in subsequent transformation described below.

(B) Transformation

About $10^8$ spores of *Streptomyces lividans* TK24 were inoculated in a 250 ml Erlenmeyer flask (containing spring) containing 25 ml of YEME+34% sucrose medium the same as that used in Example 3 (containing 5 mM $MgCl_2$, and 0.5% glycine but containing to thiopeptine), and cultivated by shaking culture at 28° C. for 32 hours.

Mycelia were collected by centrifugation and washed with 10 ml of a 10.3% sucrose solution. Thereafter, the mycelia were well suspended in 4 ml of P medium containing 1 mg/ml of lysozyme. P medium was prepared by mixing 10.3 g of sucrose, 0.025 g of $K_2SO_4$, 0.202 g of $MgCl_2.6H_2O$, 0.2 ml of a trace metal solution*, and deionized water to make 80 ml, and sterilizing the resulting mixture at 120° C. for 15 minutes, and then adding thereto 1 ml of 0.5% $KH_2PO_4$, 10 ml of 3.68% $CaCl_2.2H_2O$ and 10 ml of TES {2-[tris(hydroxymethyl) methyl]aminoethanesulfonic acid} buffer (0.25M, pH 7.2), each having had been sterilized separately in advance.
*trace metal solution contained in 1 liter the following salts: 40 mg of $ZnCl_2$, 200 mg of $FeCl_3.6H_2O$, 10 mg of $CuCl_2.2H_2O$, 10 mg of $MnCl_2.4H_2O$, 10 mg of $Na_2B_4O_7.10H_2O$, and 10 mg of $(NH_4)_6Mo_7O_{24}.4H_2O$.

After incubation, remaining mycelia which didn't form protoplasts were removed by cotton filtration. The protoplasts were collected by centrifugation (3,000 rpm, 10 minutes) and they were suspended again in P medium in a population of 3 to $4 \times 10^7$ protoplasts/100 μl. The aforementioned plasmid DNA solution (10 μl) was added to the suspension, and transformation was performed in the presence of 25% PEG 1000 (produced by BDH Chemical Co.).

After being washed with P medium, the transformed protoplasts were suspended again in 1 ml of P medium. A portion (0.1 ml) of the suspension was inoculated on an R2YE agar plate, and cultivated at 28° C. for 16 hours. After the cultivation, a soft agar medium containing thiopeptine was overlayed on the plate 30 that the final concentration of thiopeptine was 50 μg/ml, and cultivation was continued at 28° C. for 72 hours. R2YE agar plate was prepared by dissolving 10.3 g of sucrose, 0.025 g of $K_2SO_4$, 1.012 g of $MgCl_2.6H_2O$, 1 g of glucose. 0.01 g of Difco casamino acid, and 2.2 g of bacto-agar in 80 ml of distilled water, followed by sterilizing the solution at 120° C. for 15 minutes, adding thereto 0.2 ml of the aforementioned trace metal solution, 1 ml of 0.5% $KH_2PO_4$, 8 ml of 3.68% $CaCl_2.2H_2O$, 1.5 ml of 20% L-proline, 10 ml of TES buffer (0.25M, pH 7.4), 0.5 ml of 1N NaOH, and 5 ml of 10% yeast extract, each having had been sterilized in advance, and pouring 20 ml aliquots of the resulting mixture into plastic s dishes having a diameter of 9 cm. Thereafter, the dishes were dried in a clean bench for about 2 hours. On the other hand, as the soft agar medium was used a medium prepared by mixing 8 g of Nutrient broth, 3 g of bactoagar and distilled water to make 1 liter, and sterilizing the mixture at 120° C. for 15 minutes.

(C) Separation of Transformed Strains Having an Acylation Activity

Of about 1,000 transformed strains, about 200 strains were selected at random and inoculated on an agar medium composed of 1% glucose, 0.5% yeast extract, 1% malt extract, pH 7.2, 1.5% bacto-agar, and 50 μg/ml of thiopeptine, and cultivated at 28° C. for 4 days.

A soft agar medium containing leucomycin $A_1$ was overlayed on the agar medium so that the final concentration of leucomycin $A_1$ became 500 μl/ml, and cultivation was continued for 48 hours. The center of a growing colony was punched out with a cork borer having a diameter of 6 mm, and the agar piece thus obtained was placed on silica gel TLC plate (produced by Whatman, LK6DF), and air-dried.

After developing the plate in a developer composed of n-hexane:benzene:methanol:ethyl acetate=30:10:25:8:20, and product spots were tested by color development with sulfuric acid to try to detect 3-acylated leucomycin $A_1$. As a result, it was found that from among about 200 transformed strains, *Streptomyces lividans* 53A strain (hereafter, referred to as "strain 53A") produced leucomycin $A_3$, i.e., 3-O-acetyl leucomycin $A_1$. The leucomycin produced by the strain 53A was identified to be leucomycin $A_3$ from results of analyses of TLC, HPLC, UV spectrum, NMR spectrum, antibacterial spectrum and the like.

This strain 53A was internationally deposited under Budapest Treaty at Fermentation Research Institute, Agency of Industrial Science and Technology, Ministry of International Trade and Industry, Japan, at 1-3, Higashi 1-Chome, Tsukuba City, Ibaragi Prefecture, Japan under International Deposition No. FERM BP-2893.

Figure 3:
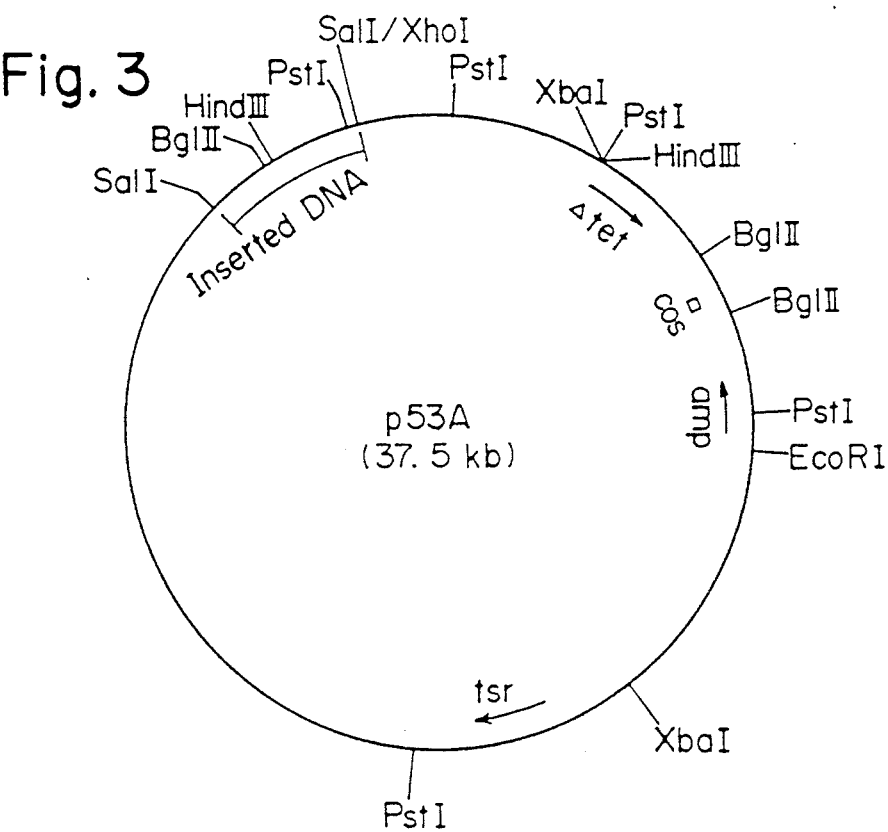
FIG. 3 is a restriction enzyme cleavage site and function map of plasmid p53A.

A plasmid was isolated from the strain 53A substantially by the method described in Example 3 to obtain plasmid p53A. This plasmid had inserted therein about 3.2 kb foreign DNA. FIG. 3 shows restriction enzyme cleavage sites and function map. The cleavage sites shown do not cover all the cleavage sites but as may as possible a site were indicated insofar as they were able to be characterized.

EXAMPLE 5

(A) Confirmation of 3-Acylation Activities of Strain 53A and of *S. lividans* retransformed by p53A Strain 53A or pA53-retransformed strain was transplanted in a circle of 2 cm in diameter on an agar medium (1% glucose, 0.5% bacto-yeast extract, 1% malt extract, and 1.5% bacto-agar to adjust pH at 7.2 and adding thereto 5 μg/ml of thiopeptine), and cultivated at 28° C. for 4 days. Then, 2 ml of soft agar containing leucomycin $A_1$ was overlayed on the agar medium so that the final concentration of leucomycin $A_1$ became 500 μg/ml.

After cultivation at 28° C. for 2 days, the central portion of the colony which grew was punched out using a cork borer, and the agar piece thus extracted was placed in an Eppendorf tube and broken to minute pieces with a plastics stick. To the minute pieces was added 50 μl of toluene and stirred vigorously for extraction. After centrifugation (16,000 rpm, 5 minutes), toluene layer, i.e., the upper layer, was collected and subjected to thin layer chromatography (TLC). As the TLC plate was used Art5715 produced by Merck Inc. The developer was the same as that used in Example 4.

After the development, the plate was dried, and sports were confirmed by color development which was performed by heating the plate at 105° C. for 5 minutes, after immersion in 10% $H_2SO_4$. Leucomycin $A_1$ had an Rf (relative mobility) value of 0.49. In the toluene extract of strain 53A or retransformed strain, there was observed a spot of leucomycin $A_3$ (a derivative of leucomycin $A_1$ whose 3-OH is acetylated) at Rf=0.60 in addition to that of unmodified leucomycin $A_1$. No production of 3-acylated derivative of leucomycin $A_1$ was observed in control strains which had not been transformed with plasmid p53A (for example, a transformed strain with vector pIHY-17).

(B) Confirmation of Leucomycin $A_3$

*S. lividans* 53A strain was cultivated by shaking culture in 1 liter of TSB (trypticase soy broth) medium containing 5 μg/ml of thiopeptine at 28° C. (using then 500 ml-flasks each containing 100 ml of medium, each flask being inoculated with a platinum loopful of strain 53A), and on day 3 leucomycin $A_1$ was added thereto (final concentration: 200 μg/ml). On day 4, the culture medium was extracted with 500 ml of ethyl acetate at pH 9.0, and dissolved again in 500 ml of a 0.01M $KH_2PO_4$ solution (adjusted to pH 3.0 with HCl), $NaHCO_3$ was added to adjust the solution to pH 9.0 again, followed by extracting with 500 ml of ethyl acetate. After evaporating it to dryness in a vacuum evaporator, the extract was dissolved in 2 ml of methanol. The whole solution was injected into HPLC. HPLC was conducted using column YMC-Pack S-3431-15 ODS (produced by Yamamura Kagaku Co.) under the conditions of room temperature and flow rate of 5 ml/min, with the mobile phase being composed of 1 volume of a mixture of 0.1M $NaH_2PO_4$ and 0.3M $NaClO_4$, adjusted to pH 2.5 with phosphoric acid, 2 volumes of methanol.

Specific peak detected at UV 230 nm (retention time: 80 minutes) was taken out. After removing methanol in the solution in a vacuum evaporator, the solution was adjusted to pH 9.0 with NaOH and extracted with ethyl acetate. The extract was evaporated to dryness in a vacuum evaporator, and then dissolved in chloroform. The chloroform solution was evaporated to dryness again to obtain 2 mg of white powder. The physical and chemical properties of the substance were examined, and results obtained are shown below.

| TLC (Merck Art5715 was used) | |
|---|---|
| Material | Rf value |
| Leucomycin A1 | 0.49 |
| Leucomycin A3 | 0.60 |
| Product of *S. lividans* 53A | 0.60 |
| (Developer solution: n-hexane:acetone:benzene: methanol:ethyl acetate = 30:10:25:8:20) | |

UV Absorption Peak $\lambda_{max}^{EtoH}(E_{1\ cm}^{1\%})$: 232 (320)

$^1$H-NMR (400 MHz, CDCl3, TDS standard)
0.97 (d, 6H, J=6.6 Hz, 4"-O—COCH$_2$CH(C$\underline{H}_3$)$_2$
2.26 (s, 3H, 3-O—COC$\underline{H}_3$)
2.51 (s, 6H, 3'-N(C$\underline{H}_3$)$_2$)
3.52 (s, 3H, 4-OC$\underline{H}_3$)
4.42 (d, 1H, J=7.3 Hz, H-1')
4.61 (d, 1H, J=10.3 Hz, H-4")
5.06 (d, 1H, J=2.9 Hz, H-1")
5.11 (d, 1H, J=11.0 Hz, H-3)
5.60 (dd, 1H, J=15.4 9.5 Hz, H-10)
6.06 (dd, 1H, J=11.0, 14.7 Hz, H-12)
6.58 (dd, 1H, J=11.0, 15.4 Hz, H-11)
9.62 (s, 1H, H-18)

Figure 4:
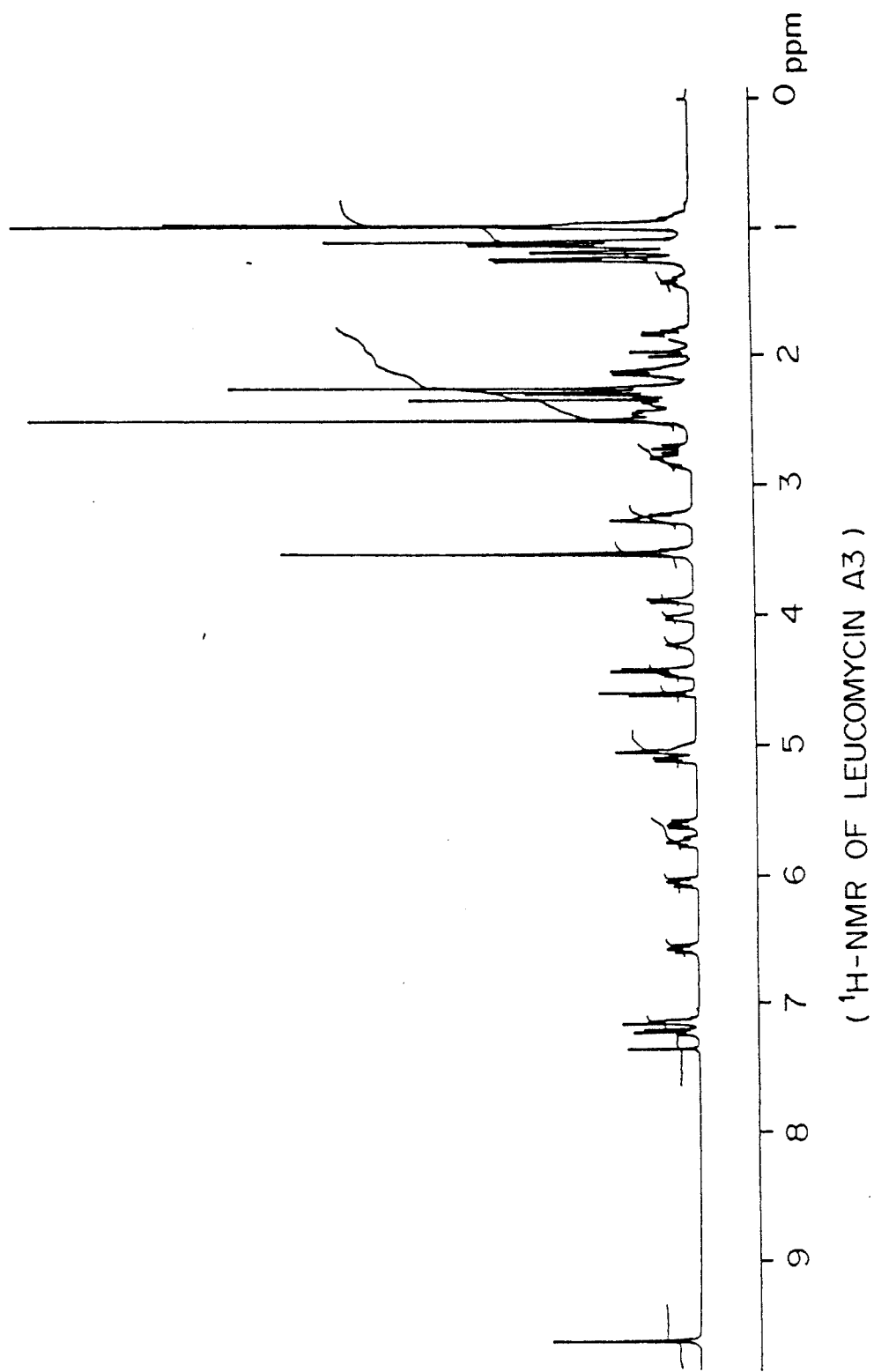
FIG. 4 is a $^1$H-NMR chart of leucomycin A$_3$.

FIG. 4 shows $^1$H-NMR spectral diagram.

The results described above were compared with the values in the literature [cf. S. Omura et al., The journal of Antibiotics, Vol. 23, p. 511-513 (1970)] and the compound was identified to be leucomycin $A_3$.

EXAMPLE 6

Construction of pMAA2 and pMAA3

P53A (cf. FIG. 3) (50 μg) was digested with SphI and subjected to electrophoresis on TAE buffer/0.8% agarose gel, and two fragments near 2 kb were extracted and purified as a mixture using GENE CLEAN KIT (Bio101). The mixture of the fragments (0.6 μg) and 0.2 μg of SphI-linearized DNA of *E. coli* vector pUC19 were dissolved in 18 μl of TE buffer, and 2 μl of 10×ligation buffer and 300 units of T4DNA ligase (Nippon Gene) were added thereto. The mixture was incubated at 16° C. for 4 hours. *E. coli* JM103 competent cells were transformed with 10 μl of the reaction mixture and the cells were inoculated on an ampicillin-Xgal medium (1% bacto-tryptone, 0.5% bactoyest extract, 1% NaCl, 1.5 g of bacto-agar, pH 7.4, after autoclaving, 50 mg/ml of ampicillin, 0.5 mM IPTG, and 0.01% Xgal being added), and six white colonies, i.e., six strains which caused insertional inactivation of the lacZ gene in vector pUC19, were picked up, and plasmids were extracted on a small scale.

Figure 5:
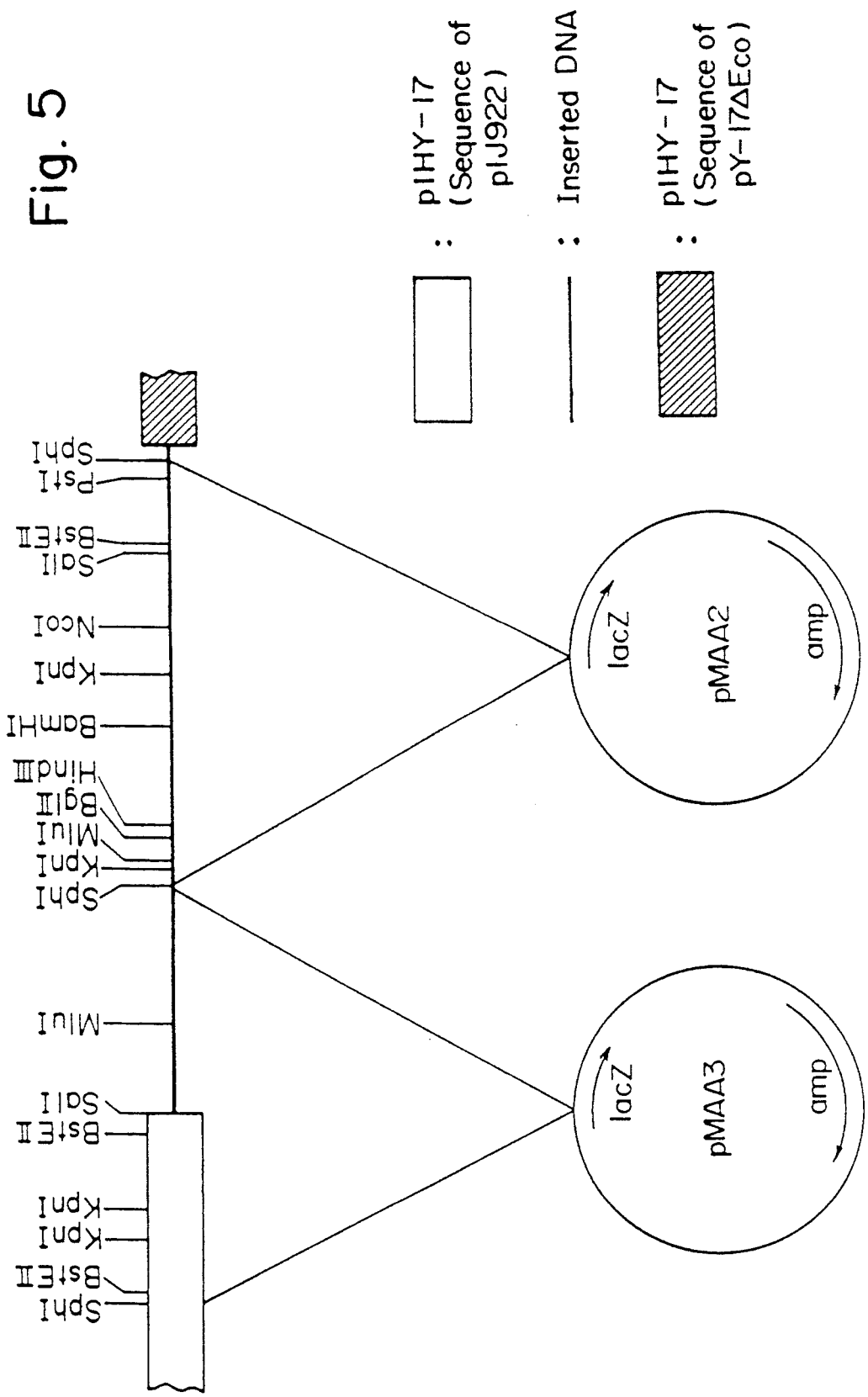
FIG. 5 is a restriction enzyme cleavage site and function map of each of plasmids pMAA2 and pMAA3.

Then, these plasmids were digested with restriction enzymes and digested fragments were subjected to electrophoresis, and electrophoretic patterns were examined to confirmation which of the two types of fragments was inserted therein. More specifically, each plasmid was reacted with BglII, and the type of the fragment contained was judged whether linearization occurred or the plasmid remained intact. As a result, it revealed that two strains contained the former type of plasmid (having one BglII cleavage site in the inserted fragment), and four strains had the latter type of plasmid (having no BglII cleavage site in the inserted fragment). One of the former type of the strains was selected and its plasmid was named pMAA2 while one of the latter type of the strains was selected and its plasmid was named pMAA3 (cf. FIG. 5).

Plasmids pMAA2 and pMAA3 sere prepared on a large scale according to the method described in Example 2. Further, restriction enzyme map of DNA fragment containing the gene acyA was prepared by precisely determining the restriction sites of the inserted fragments in these plasmids (cf. FIG. 1).

EXAMPLE 7

Determination of Base Sequence of acyA

The 3-acylation enzyme-coding gene acyA were cut out readily from plasmid p53A with restriction enzymes BamHI and SalI, and the base sequence (1810 bp) was determined using 7-Deazaseaquences version 2.0 (United Biochemical Corporation/Cleveland, Ohio, United States of America), a commercially available sequence kit. The sequence obtained is shown in FIG. 6.

The code region of acyA was found to range from 209th to 1,375th bases. Near upstream of the 5'-side of ATG, which is an initiation codon of the code region, ribosome bonding sites each composed of AAGGA were found to range from 194th to 198th bases and from 201st to 205th bases. Upstream thereof were present promoter region, i.e., TTGCCG (120th to 125th bases) corresponding to the −35 region, and CAGGAT (143rd to 148th bases) corresponding to the −10 region. FIG. 7 shows the base sequence of acyA and the amino acid sequence coded thereby.

EXAMPLE 8

Production of Acylated Tylosin (A) Preparation of pAB5

To 2 μg of recombinant plasmid pMABl (cf. EP-A-345,546) carrying the gene acyB encoding 4"-acylation enzyme for macrolides were sequentially added 18 μl of TE buffer, 2 μl of XbaI buffer having a concentration by 10 times as thick as usual (500 mM NaCl, 200 mM Tris-HCl (pH 7.9), 100 mM $MgCl_2$, 100 mM 2-mercapto-ethanol), and 1 μl (15 units) of restriction enzyme XbaI, and the mixture was allowed to react at 37° C. for 2 hours. After extracting the DNA solution with an equivalent volume of phenol/chloroform mixed solution (phenol:chloroform:isoamyl alcohol=25:25:1, containing 0.1% quinolinol saturated with TE buffer), 1/10 time the volumic quantity of a 3M sodium acetate solution (pH 5.2) and 3 times the volumic quantity of ethanol were added to the extract to precipitate DNA. The DNA thus obtained was washed with 70% ethanol and dissolved in 8 μl of TE buffer. To the resulting solution were added 1 μl of exonuclease III buffer having a concentration by 10 times as thick as usual (500 mM Tris-HCl (pH 8.0), 50 mM $MgCl_2$, 100 mM 2-mercaptoethanol) and 1 μl (50 units) of exonuclease III (Nippon Gene Co., Ltd.) were added, and the resulting mixture was reaction at 30° C. for 1 minute. Immediately thereafter, 24 μl of $H_2O$, 4 μl of nuclease S1 buffer having a concentration by 10 times as thick as usual (330 mM sodium acetate (pH 4.5), 500 mM NaCl, 0.3 mM $ZnSO_4$) and 2 ml (20 units) of nuclease S1 (Boehringer Mannheim Yamanouchi Co., Ltd.) were added to the mixture, and reacted at room temperature for 15 minutes. After completion of the reaction, DNA was purified by the extraction with phenol/chloroform and precipitation with ethanol in the same manner as described above, and the purified DNA was dissolved in 23 μl of TE buffer. To the resulting solution were added 3 μl of M buffer having a concentration by 10 times as thick as usual (500 mM NACl, 100 mM Tris-HCl (pH 7.5), 100 mM $MgCl_2$, 10 mM dithiothreitol) and 3 μl of dNTP mixed solution (an aqueous mixed solution containing each 0.5 mM of dGTP, dCTP, dATP, and dTTP) as well as 1 μl (4 units) of DNA polymerase (large fragment, Takara Shuzo Co., Ltd.), followed by reaction at 37° C. for 30 minutes to obtain DNA with blunt ends. After purifying the DNA by extraction with phenol/chloroform and precipitation with ethanol as described above, the DNA thus obtained was dissolved in 10 μl of TE buffer to prepare a vector solution. On the other hand, 100 μg of the recombinant plasmid p53A obtained in Example 4 was digested with restriction enzymes SalI and BamHI and 1.8 kb DNA fragment containing acyA was separated and purified using GENE CLEAN (Bio101) to obtain 4 μg of the objective fragment. The DNA fragment thus obtained was treated under the same conditions as above in order to obtain DNA with blunt ends, and purified by extraction with phenol/chloroform and precipitation with ethanol. The DNA thus obtained was dissolved in TE buffer to obtain a TE solution (0.2 μg/μl). To 2.5 μl (0.5 μg) of the TE solution were sequentially added 2.5 μl (0.5 μg) of the aforementioned vector solution, 13 μl of purified water, 2 μl of a ligation buffer having a concentration by 10 times as thick as usual (500 mM Tris-HCl (pH 7.9), 100 mM $MgCl_2$, 200 mM dithiothreitol, 100 mM ATP) and 1 μl (300 units) of T4DNA ligase (Nippon Gene Co., Ltd.), and the resulting mixture was reacted at 16° C. for 15 hours. A portion (2 μl) of the reaction mixture was used to transform 100 ml of *E. coli* JM103 competent cells according to the method described by Maniatis et al., *Molecular Cloning*, Cold Spring Harbor Laboratory.

Figure 8:
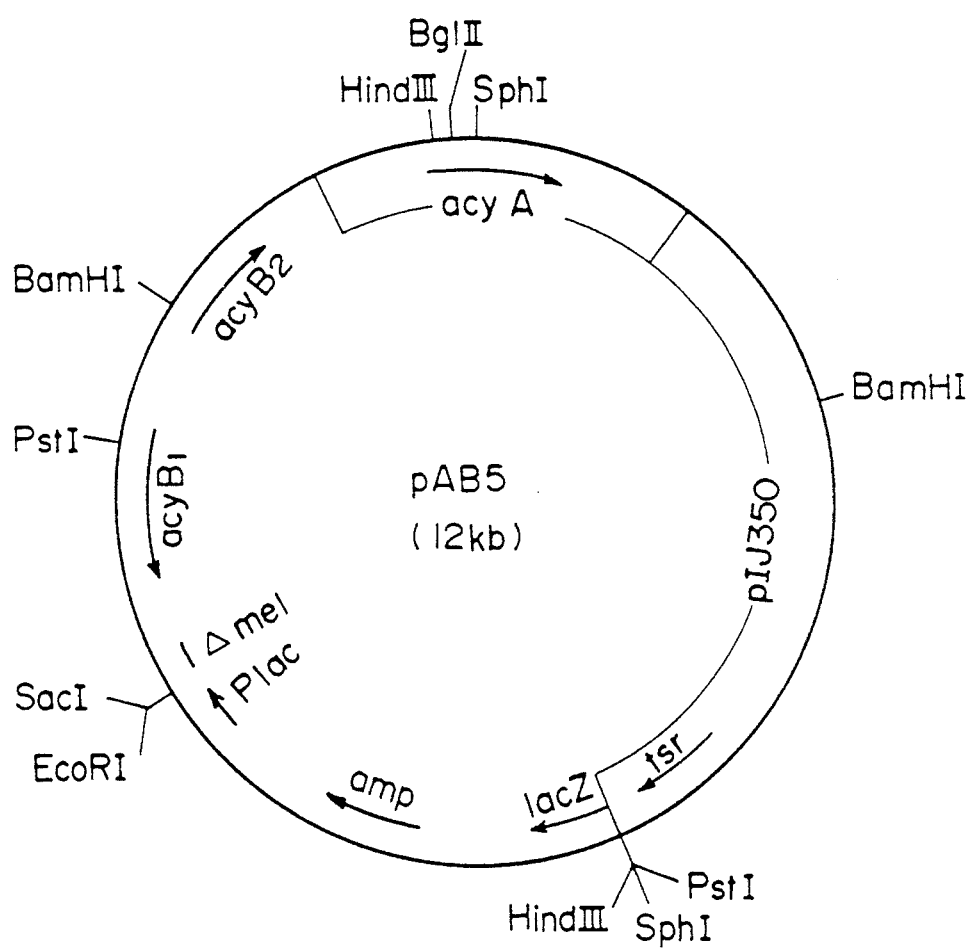
FIG. 8 is a restriction enzyme cleavage site and function map of plasmid pAB5.

Plasmids obtained from the transformants were examined by electrophoresis on agarose gel. As a result, plasmid pA85 having an inserted fragment of about 1.8 kb and a structure shown in FIG. 8 was obtained.

(B) pAB10, pAB10ΔB1

Figure 9:
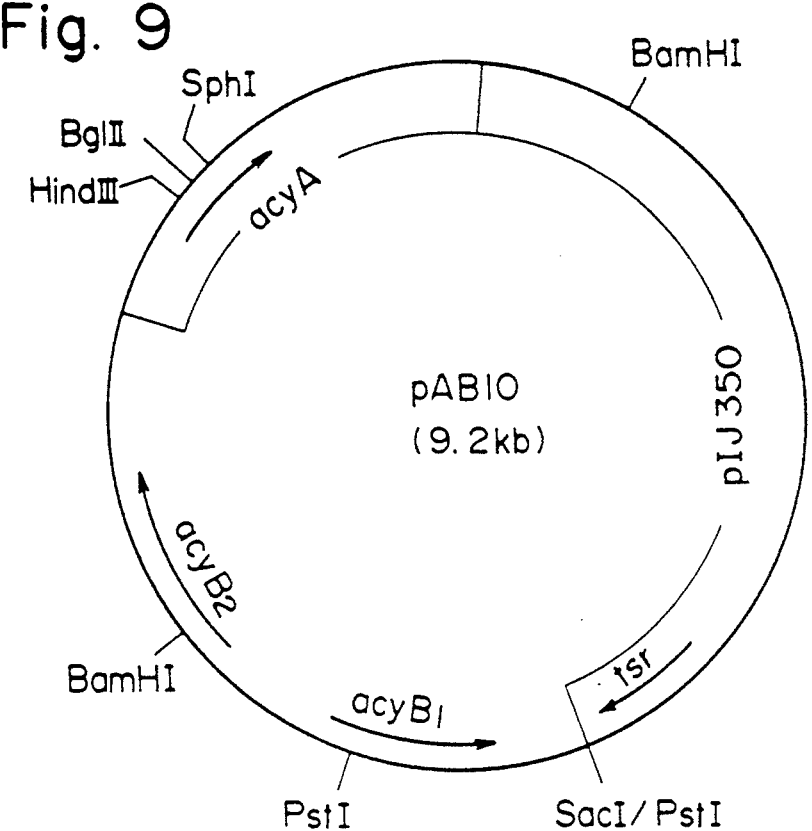
FIG. 9 is a restriction enzyme cleavage site and function map of plasmid pAB10.
Figure 10:
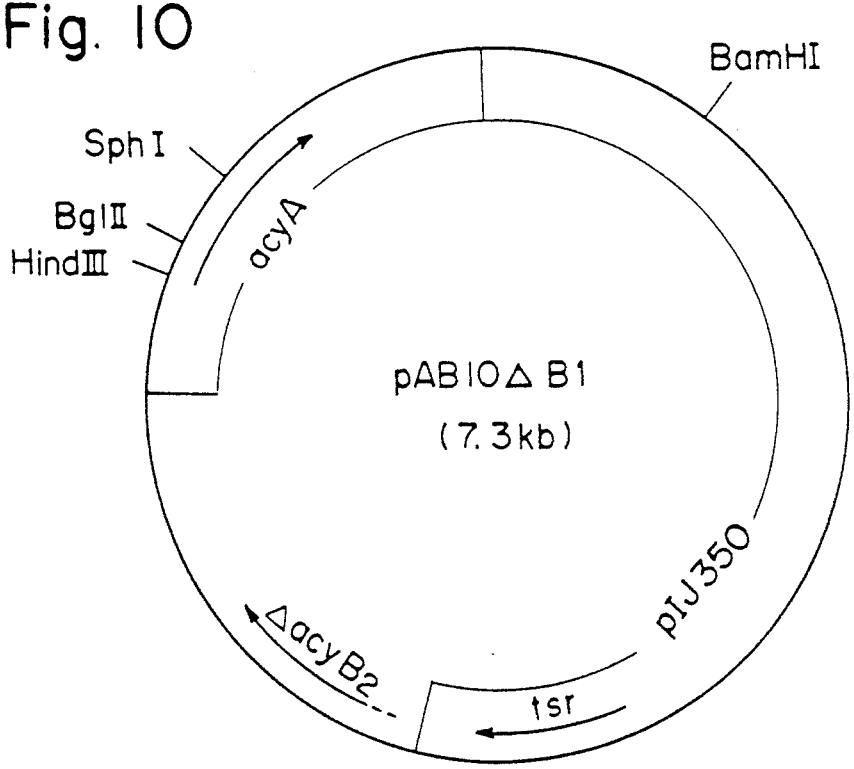
FIG. 10 is a restriction enzyme cleavage site and function map of plasmid pAB10ΔB1.

Plasmid pAB5 (10 μg) was completely digested with restriction enzyme SacI, and extracted with phenol/chloroform and precipitated with ethanol to purify the resulting DNA fragments. The DNA fragments were partially digested with restriction enzyme PstI to obtain various fragments, from which about 9.2 kb DNA fragment formed as a result of cutting off only the pUC18-derived DNA fragment was separated by electrophoresis on 0.8% agarose gel, and recovered and purified using GENE CLEAN (Bio101). The DNA fragment thus obtained was dissolved in 22 μl of TE buffer. To the resulting solution were added 3 μl of T$_4$-polymerase buffer having a concentration by 10 times as thick as usual (700 mM Tris-HCl (pH 7.4), 100 mM MgCl$_2$, 50 mM dithiothreitol) and 3 μl of dNTP mixed solution (an aqueous mixed solution containing each 0.5 mM of dGTP, dCTP, dATP, and dTTP) as well as 2 μl (4.8 units) of T$_4$DNA polymerase (Toyobo Co., Ltd.), followed by reaction at 37° C. for 30 minutes to obtain DNA with blunt ends. After purifying the DNA by extraction with phenol/chloroform and precipitation with ethanol as described above, the DNA thus obtained was dissolved in 45 μl of TE buffer. To the resulting solution were added 5 μl of ligation buffer having a concentration by 10 times as thick as usual 1 μl (300 units) of T$_4$DNA ligase (Nippon Gene Co., Ltd.), and reaction was performed at 16° C. for 15 hours to effect self-cyclization. After completion of the reaction, protoplast of *Streptomyces lividans* TK24 were transformed with 20 μl of the reaction mixture. From the transformants, clones with plasmids of which pUC18 region was completely deleted were selected by difference in electrophoretic pattern of the plasmids from intact ones. Among the clones thus selected, there were obtained pAB10 having a structure shown in FIG. 9, and pAB10ΔB1 having a structure shown in FIG. 10. The both plasmids are common in that they correspond to pAB5 of which pUC18 region is deleted but in the latter (pAB10ΔB1) deletion proceeded to the region of the 4"-acylation enzyme-coding gene acyB as a result of side reaction by the enzyme, resulting in the fact the transformed strains transformed therewith cannot produce a 4"-acylation enzyme.

(C) Production of 3-O-Acetyltylosin

A platinum loopful of a slant culture medium of *Streptomyces fradiae* ATCC 19609 was inoculated in a 250 ml-Erlenmeyer flask containing spring) containing 20 ml of GPY medium (1.0% glucose, 0.4% polypeptone, 0.4% yeast extract, 0.05% MgSO$_4$.7H$_2$O, 0.1% K$_2$HPO$_4$, and 0.05% glycine, pH 7.2), and cultivated by shaking culture 28° C. for 48 hours. The culture medium (0.5 ml) was inoculated in a 250 ml-Erlenmeyer flask (containing spring) containing 25 ml of YEME+15% sucrose medium (containing 5 mM MgCl$_2$ and 0.5% glycine) described in Example 4, and cultivated by shaking culture at 28° C. for 40 hours. After collecting mycelia by centrifugation (3,000 rpm, 15 minutes), and washing it with 10 ml of 10.3% sucrose, the mycelia were suspended well in 4 ml of P medium containing 1 mg/ml of lysozyme, and reaction was performed at 30° C. for 1 hour. The composition of P medium itself was described in Example 4. After completion of the reaction, mycelia which remained was removed by filtration with cotton, and protoplasts were collected by centrifugation (3,000 rpm, 10 minutes) and the protoplasts thus obtained were suspended in P medium to a population of 3×10$^9$/100 μl. To the suspension was added 10 μl of the aforementioned pAB10ΔB1 solution (15 μg/10 μl), and transformation was performed in the presence of 25% PEG1000 (BDH Chemical Co.). After washing them with P medium, the transformed protoplasts were suspended again in 1 ml of P medium. A portion (0.1 ml) thereof was inoculated on R3 medium (13.5 g of sucrose, 0.05 g of KCl, 1.0 g of glucose, 0.4 g of polypeptone, 0.4 g of yeast extract, 0.573 g of TES buffer. 6.1 ml of 10% MgCl$_2$ solution, 2.0 g of bacto-agar, and 100 ml of distilled water; after sterilization by auto-claving, 1.0 ml of KH$_2$PO$_4$ (0.5%), 0.3 ml of CaCl$_2$ (5M), and 1.8 ml of NaOH (1N) being added thereto), and cultivated at 28° C. for 16 hours. After the cultivation, soft agar medium containing thiopeptine was overlayed on the culture medium so that the final concentration of thiopeptine became 5 μg/ml or 25 μg/ml, and cultivation was continued at 28° C. for 7 days. The soft agar medium was prepared by mixing 8 g of Nutrient broth, 3 g of bacto-agar and 1 liter of distilled water, and sterilizing the mixture by autoclaving at 120° C. for 15 minutes.

Many colonies grew on the medium containing 5 μg/ml of thiopeptine while a few resistant colonies appeared on the medium containing 25 μg/ml of thiopeptine. One of the strains resistant to the 25 μg/ml medium was named *Streptomyces fradiae* AB10ΔB1 strain (hereafter, referred to as AB10ΔB1 strain), and production of acylated tylosin was tested on this strain.

In a 250 ml-Erlenmeyer flask (containing coil) containing 50 ml of a production medium (0.5% soluble starch, 5% glucose, 0.5% yeast extract, 1.0% malt extract, and 5 μg/ml of thiopeptine) was inoculated a platinum loopful of AB10ΔB1 strain, and cultivated by shaking culture at 28° C. for 21 days. Then, to a portion (1 ml) of the culture medium were added 0.2 g of K$_2$HPO$_4$ and 0.2 ml of toluene, and the mixture was stirred vigorously to effect extraction. After centrifugation (3,000 rpm, 10 minutes), the toluene layer, which is an upper layer, was taken out and subjected to thin layer chromatography. As the thin layer chromatography plate was used Art 5715 (produced buy Merck Co.) and the developer used was ethyl acetate (75 ml):diethylamine (1.5 ml):water (1.5 ml):methanol (0.75 ml). After drying it, the plate was analyzed at 280 nm using Chromato Scanner (CS-930, produced by Shimazu Seisakusho), and the positions of spots were confirmed by color development by immersing the plate in 10% H solution and heating it at 105° C. for 5 minutes. Tylosin had an Rf (relative mobility) value of 0.62 while the product by the transformed strain contained 3-acetyl-tylosin at Rf=0.68 in addition to tylosin.

On the other hand, control strain which had not been transformed with plasmid pAB10ΔB1 produced no 3-acetyltylosin.

(D) Confirmation of 3-O-Acetyltylosin

The aforementioned culture medium (1 liter, i.e., 20 tubes each containing 50 ml of the culture medium)

were extracted with ethyl acetate at pH 8.5, and transferred in 200 ml of acidic water (0.01N HCl) and adjusted again to pH 8.5, followed by extraction with 50 ml of ethyl acetate. The extract was concentrated to 10 ml, and 2 ml thereof was spotted in the form of a band on each of five thin layer chromatography plates (Art 5715, produced by Merck Co.), and developed with the aforementioned developer. After air-drying, the silica gel corresponding to the spot of Rf=0.68 was cut out, and extracted with 10 ml of acetone. The extract was evaporated to dryness in a vacuum evaporator to obtain 20 mg of white powder. The substance was examined for its physical chemical properties. Results obtained are shown below.

| | |
|---|---|
| Molecular Weight: | 958 (Chemical impact mass analysis gave a dehydrated ion peak of 941.) |
| Optical Rotation $[\alpha]_D^{24}$(c1.0, MeOH): | 33.9 |
| UV Absorption Peak $\lambda_{max}^{EtOH}(E_{1\ cm}^{1\%})$: | 282 (235) |

$^1$H-NMR ($\delta$, ppm):
1.8 (12-CH$_3$), 2.14 (3-OCOCH$_3$), 2.5 (N(CH$_3$)$_2$), 3.5 (3″=OCH$_3$), 3.6 (2‴OCH$_3$), 4.15 (H1′), 4.55 (H1‴), 4.60 (H4″), 5.05 (H1″), 5.95 (H12), 6.25 (H10), 7.3 (H11), 9.7 (CHO).

Figure 11:
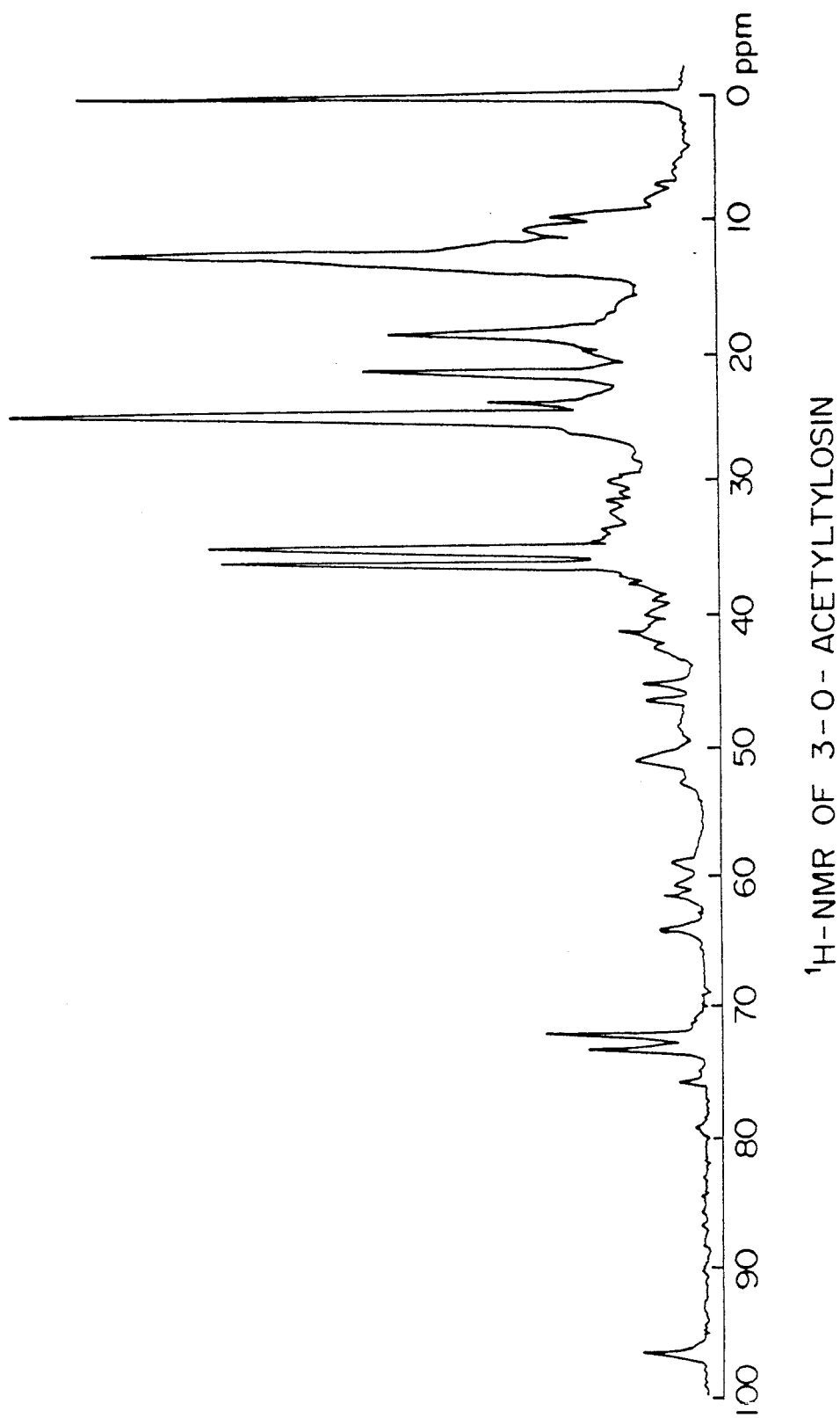
FIG. 11 is a $^1$H-NMR chart of 3-O-acetyltylosin.

FIG. 11 shows a $^1$H-NMR chart.

The above-described results were compared with the values on the literature (U.S. Pat. No. 4,092,473, and Journal of Antibiotics, Vol. 33, p. 1,300–1,308 (1980)), and the compound was identified to be 3-O-acetyltylosin.

(E) Transformation with pAB10

In the same manner as in (C) above, a platinum loopful of a slant culture of Streptomyces fradiae ATCC 19609 was cultivated, and protoplasts were made therefrom using lysozyme. Transformation of the plasmids was performed using as the plasmid pJ702 (prepared from Streptomyces lividans ATCC 35287 by the method of Hopwood (Genetic Manipulation of Streptomyces: A Laboratory Manual, John Innes Foundation, Norwich, England, (1985)), and the transformed strain was converted into protoplast again in the same manner as in (C) above. After regeneration, a strain losing of pIJ702 was obtained. The strain was named S. fradiae C-1.

S. fradiae C-1 thus obtained was cultivated in the same manner as in (C) above, and 10 μl of the aforementioned plasmid pAB10 solution (15 μg/10 μl) was added thereto, and transformation was practiced in the presence of 25% PEG1000 (produced by BDH Chemical Co.).

The protoplasts thus transformed were washed with P medium, and then suspended again in 1 ml of P medium. A portion (0.1 ml) of the suspension was inoculated on R3 medium (13.5 g of sucrose, 0.05 g of KCl, 1.0 g of glucose, 0.4 g of polypeptone, 0.4 g of yeast extract, 0.573 g TES buffer, 6.1 ml of 10% MgCl$_2$ solution, 2.0 g of bacto-agar, and 100 ml of distilled water; after sterilization by autoclaving, 1.0 ml of KH$_2$PO$_4$ (0.5%), 0.3 ml of CaCl$_2$ (5M), and 1.8 ml of NzOH (1N) being added thereto), and cultivated at 28° C. for 16 hours. After the cultivation, soft agar medium containing thiopeptine was overlayed on the culture medium so that the final concentration of thiopeptine became 5 μm/ml or 25 μg/ml, and cultivation was continued at 28° C. for 7 days. The soft agar medium was prepared by mixing 8 g of Nutrient broth, 3 g of bacto-agar and 1 liter of distilled water, and sterilizing the mixture by autoclaving at 120° C. for 15 minutes.

Many colonies grew on the medium containing 5 μg/ml of thiopeptine while a few resistant colonies appeared on the medium containing 25 μg/ml of thiopeptine. One of the strains resistant to the 25 μg/ml medium was named Streptomyces fradiae AB10 strain (hereafter, referred to as AB10 strain), and production of acylated tylosins was tested on this strain.

In a 250 ml-Erlenmeyer flask (containing coil) containing 50 ml of a production medium (0.5% soluble starch, 5% glucose, 0.5% yeast extract, 1.0% malt extract, and 5 μg/ml of thiopeptine) was inoculated a platinum loopful of AB10 strain, and cultivated by shaking culture at 28° C. for 7 days. Then, to a portion (1 ml) of the culture medium were added 0.2 g of K$_2$HPO$_4$ and 0.2 ml of toluene, and the mixture was stirred vigorously to effect extraction. After centrifugation (3,000 rpm, 10 minutes), the toluene layer, which is an upper layer, was taken out and subjected to thin layer chromatography. As the thin layer chromatography plate was used Art 5715 (produced buy Merck Co.) and the developer used was ethyl acetate (75 ml):diethylamine (1.5 ml):water (1.5 ml):methanol (0.75 ml). After drying it, the plate was analyzed at 280 nm using Chromato Scanner (CS-930, produced by Shimazu Seisakusho), and the positions of spots were confirmed by color development by immersing the plate in 10% H$_2$SO$_4$ solution and heating it at 105° C. for 5 minutes. Tylosin had an Rf (relative mobility) value of 0.62 while the product by the transformed strain contained 3-O-acetyl-4″-O-isovaleryltyrosine at Rf=0.82 in addition to tylosin. The S. fradiae AB10 strain was deposited internationally deposited under Budapest Treaty at Fermentation Research Institute, Agency of Industrial Science and Technology, Ministry of International Trade and Industry, Japan, at 1-3, Higashi 1-Chome, Tsukuba City, Ibaragi Prefecture, Japan under International Deposition No. FERM BP-3212.

On the other hand, control strain which had not been transformed with pasmid pAB10 produced no 3-O-acetyl-4″-O-isovaleryltylosin.

(D) Confirmation of 3-O-Acetyl-4″-O-isovaleryltylosin

The aforementioned culture medium (1 liter, i.e., 20 tubes each containing 50 ml of the culture medium) were extracted with ethyl acetate at pH 8.5, and transferred in 200 ml of acidic water (0.01N HCl) and adjusted again to pH 8.5, followed by extraction with 50 ml of ethyl acetate. The extract was concentrated to 10 ml, and 2 ml thereof was spotted in the form of a band on each of five thin layer chromatography plates (Art 5715, produced by Merck Co.), and developed with the aforementioned developer. After air-drying, the silica gel corresponding to the spot of Rf=0.82 was cut out, and extracted with 10 ml of acetone. The extract was evaporated to dryness in a vacuum evaporator to obtain 5 mg of white powder. The substance was examined for its physical chemical properties. Results obtained are shown below.

| | |
|---|---|
| Molecular Weight: | 1,042 (Chemical impact mass analysis gave a dehydrated ion peak of 1,025.) |
| Optical Rotation $[\alpha]_D^{24}$(c1.0, MeOH): | −34.3 |
| UV Absorption Peak $\lambda_{max}^{EtOH}(E_{1\ cm}^{1\%})$: | 282 (222) |

-continued

1H-NMR (δ, ppm)
0.97 (OCCH$_2$CH(CH$_3$)$_2$), 1.8 (12-CH$_3$), 2.14 (3-OCOCH$_3$), 2.28 (OCCH$_2$CH(CH$_3$)$_2$), 2.5 (N(CH$_3$)$_2$), 3.5 (3''-OCH$_3$), 3.6 (2'''OCH$_3$), 4.15 (H1'), 4.55 (H1'''), 4.60 (H4''), 5.05 (H1''), 5.95 (H12), 6.25 (H10), 7.3 (H11), 9.7 (CHO)

Figure 12:
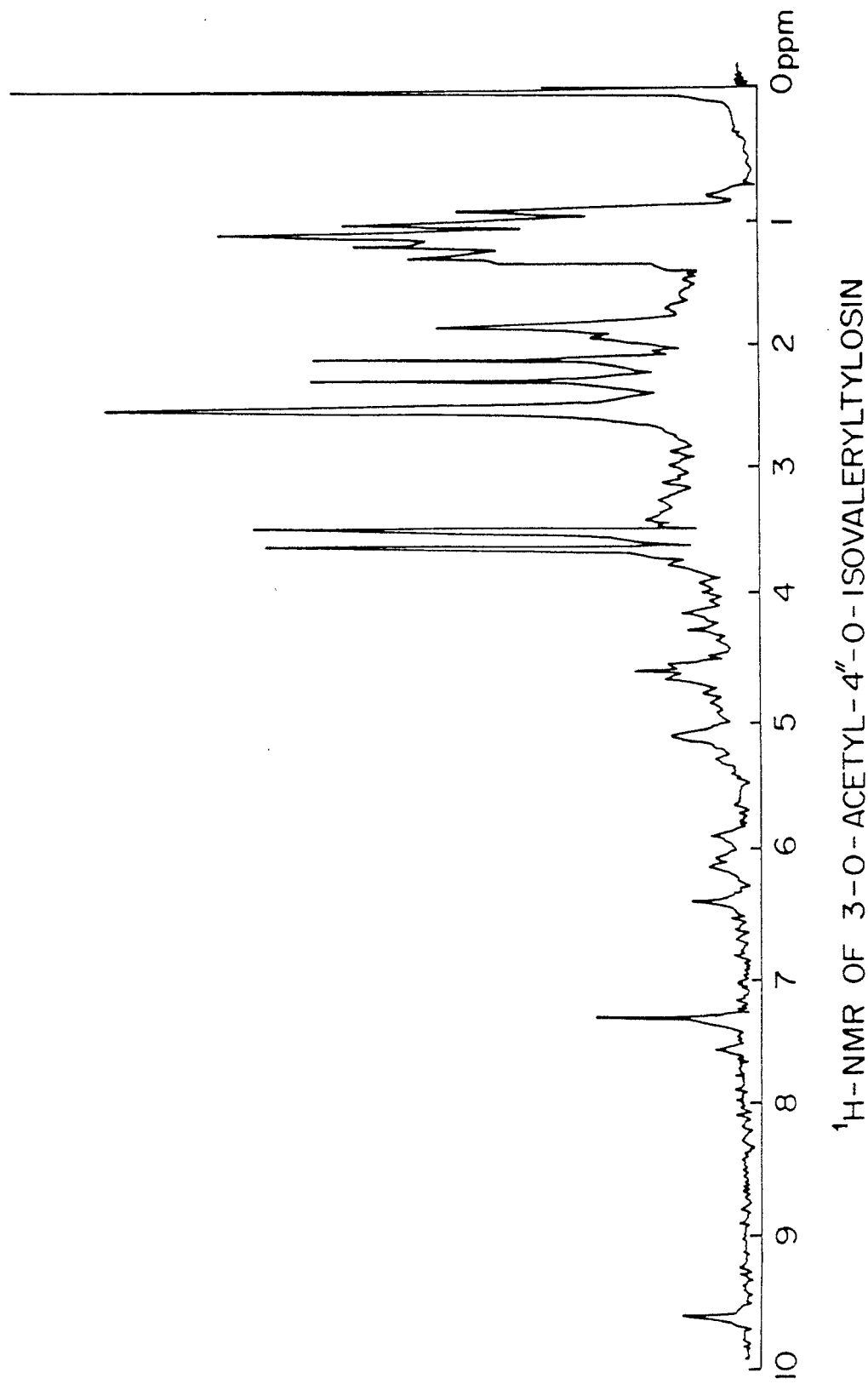
FIG. 12 is a $^1$H-NMR chart of 3-O-acetyl-4"-O-isovaleryltylosin.
Figure 15:
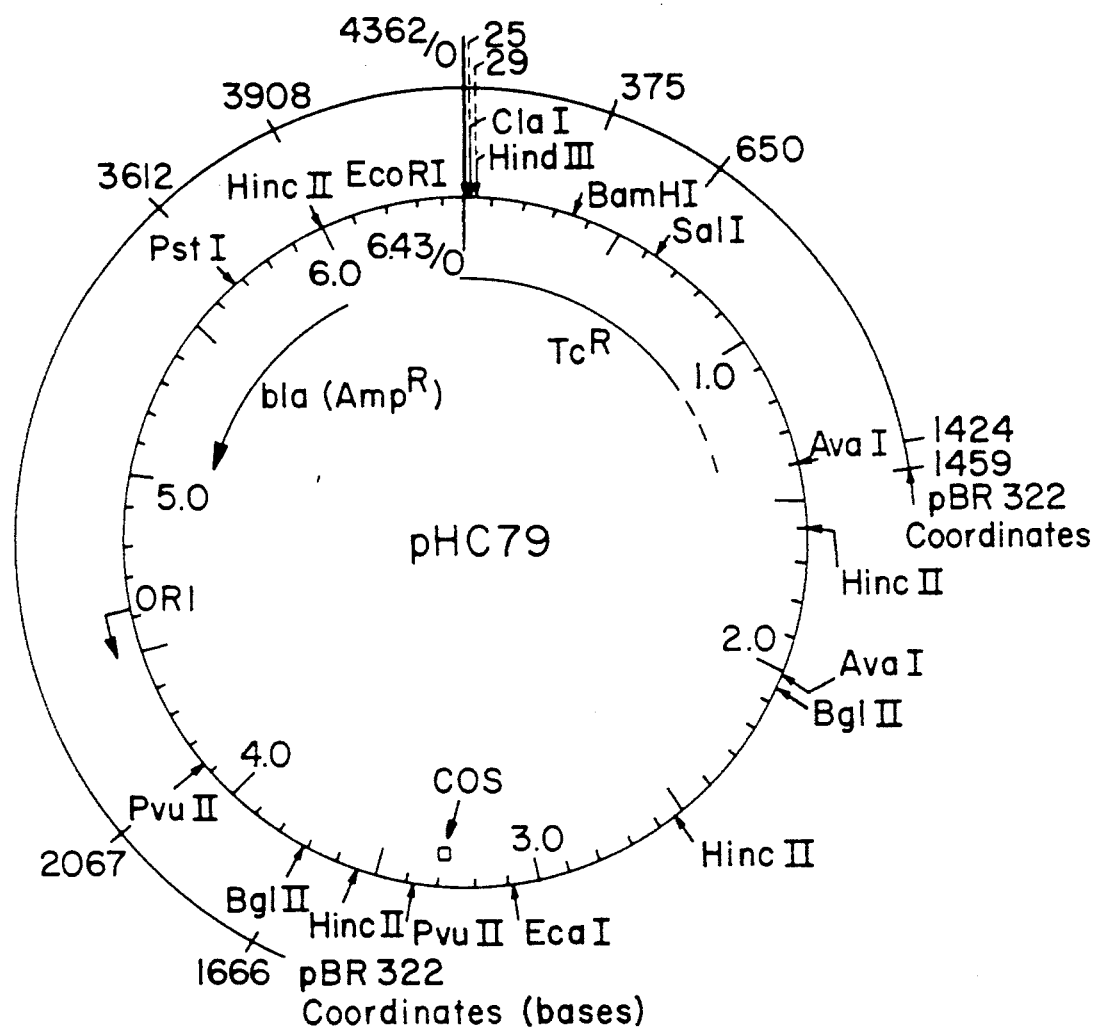
FIG. 15 is a restriction enzyme cleavage site and function map of plasmid pHC79.

FIG. 12 shows a $^1$H-NMR chart.

The above-described results were compared with the data by Okamoto et al. (R. Okamoto et al., The Journal of Antibiotics, Vol. 33, p. 1,300–1,308 (1980)), and the compound was identified to be 3-O-acetyl-4''-O-isovaleryltylosin.

What is claimed is:

1. A purified and isolated DNA consisting essentially of a gene, acyA, encoding a 3-acylation enzyme for macrolide antibiotics, said DNA being derived from a strain belonging to the genus Streptomyces, having a size of about 1.8 kb, and having a DNA base sequence shown in a restriction enzyme map shown in FIG. 1(A) in the attached drawing, wherein said DNA encodes Seq. I.D. No. 2.

2. A purified and isolated DNA consisting essentially of a gene, acyA, encoding a 3-acylation enzyme for macrolide antibiotics, said DNA being derived from a strain belonging to the genus Streptomyces, having a size of about 1.8 kb, and having a DNA base sequence shown in a restriction enzyme map shown in FIG. 1(A) in the attached drawing, wherein said DNA is Seq. I.D. No. 1.

* * * * *